United States Patent
Lim et al.

(10) Patent No.: US 8,048,118 B2
(45) Date of Patent: Nov. 1, 2011

(54) ADJUSTABLE INTERSPINOUS PROCESS BRACE

(75) Inventors: Roy Lim, Memphis, TN (US); Thomas Carls, Memphis, TN (US); Aurelien Bruneau, Memphis, TN (US); Eric C. Lange, Collierville, TN (US); Kent M. Anderson, Memphis, TN (US); Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 906 days.

(21) Appl. No.: 11/413,980

(22) Filed: Apr. 28, 2006

(65) Prior Publication Data
US 2007/0270827 A1    Nov. 22, 2007

(51) Int. Cl.
*A61B 17/70* (2006.01)
(52) U.S. Cl. ............... 606/249; 606/248; 623/17.11
(58) Field of Classification Search ........... 606/248–249
See application file for complete search history.

(56) References Cited

U.S. PATENT DOCUMENTS

| | | |
|---|---|---|
| 624,969 A | 5/1899 | Peterson |
| 1,153,797 A | 9/1915 | Kegreisz |
| 1,516,347 A | 11/1924 | Pataky |
| 1,870,942 A | 8/1932 | Beatty |
| 2,077,804 A | 4/1937 | Morrison |
| 2,299,308 A | 10/1942 | Creighton |
| 2,485,531 A | 10/1949 | Dzus et al. |
| 2,607,370 A | 8/1952 | Anderson |
| 2,677,369 A | 5/1954 | Knowles |
| 2,685,877 A | 8/1954 | Dobelle |
| 3,065,659 A | 11/1962 | Eriksson et al. |
| 3,108,595 A | 10/1963 | Overment |
| 3,397,699 A | 8/1968 | Kohl |
| 3,426,364 A | 2/1969 | Lumb |
| 3,648,691 A | 3/1972 | Lumb et al. |
| 3,779,239 A | 12/1973 | Fischer et al. |
| 3,867,728 A | 2/1975 | Stubstad et al. |
| 4,003,376 A | 1/1977 | McKay et al. |
| 4,011,602 A | 3/1977 | Rybicki et al. |
| 4,078,559 A | 3/1978 | Nissinen |
| 4,237,875 A | 12/1980 | Termanini |
| 4,257,409 A | 3/1981 | Bacal et al. |
| 4,274,324 A | 6/1981 | Giannuzzi |
| 4,289,123 A | 9/1981 | Dunn |

(Continued)

FOREIGN PATENT DOCUMENTS

DE    2821678 A1    11/1979
(Continued)

OTHER PUBLICATIONS

"Dispositivo Intervertebrale Ammortizzante DIAM," date unknown, p. 1.
(Continued)

*Primary Examiner* — Eduardo C Robert
*Assistant Examiner* — Julianna N Harvey

(57) ABSTRACT

An adjustable interspinous process brace is disclosed and can include a superior component. The superior component can include a superior spinous process bracket that can engage a superior spinous process. Further, the adjustable interspinous process brace can include an inferior component. The inferior component can include an inferior spinous process bracket that can engage an inferior spinous process. Further, the inferior component can be movably engaged with the superior component from a retracted position to an extended position. In the extended position, a distance between the superior spinous process bracket and the inferior spinous process bracket can be increased.

14 Claims, 13 Drawing Sheets

U.S. PATENT DOCUMENTS

| | | | |
|---|---|---|---|
| 4,327,736 A | 5/1982 | Inoue | |
| 4,401,112 A | 8/1983 | Rezaian | |
| 4,499,636 A | 2/1985 | Tanaka | |
| 4,519,100 A | 5/1985 | Wills et al. | |
| 4,553,273 A | 11/1985 | Wu | |
| 4,554,914 A | 11/1985 | Kapp et al. | |
| 4,570,618 A | 2/1986 | Wu | |
| 4,573,454 A | 3/1986 | Hoffman | |
| 4,592,341 A | 6/1986 | Omagari et al. | |
| 4,599,086 A | 7/1986 | Doty | |
| 4,604,995 A | 8/1986 | Stephens et al. | |
| 4,611,582 A | 9/1986 | Duff | |
| 4,632,101 A | 12/1986 | Freedland | |
| 4,636,217 A | 1/1987 | Ogilvie et al. | |
| 4,643,178 A | 2/1987 | Nastari et al. | |
| 4,646,998 A | 3/1987 | Pate | |
| 4,657,550 A | 4/1987 | Daher | |
| 4,662,808 A | 5/1987 | Camilleri | |
| 4,686,970 A | 8/1987 | Dove et al. | |
| 4,704,057 A | 11/1987 | McSherry | |
| 4,721,103 A | 1/1988 | Freedland | |
| 4,759,769 A | 7/1988 | Hedman et al. | |
| 4,787,378 A | 11/1988 | Sodhi | |
| 4,822,226 A | 4/1989 | Kennedy | |
| 4,827,918 A | 5/1989 | Olerud | |
| 4,834,600 A | 5/1989 | Lemke | |
| 4,863,476 A | 9/1989 | Shepperd | |
| 4,886,405 A | 12/1989 | Blomberg | |
| 4,892,545 A | 1/1990 | Day et al. | |
| 4,913,144 A | 4/1990 | Del Medico | |
| 4,931,055 A | 6/1990 | Bumpus et al. | |
| 4,932,975 A | 6/1990 | Main et al. | |
| 4,936,848 A | 6/1990 | Bagby | |
| 4,969,887 A | 11/1990 | Sodhi | |
| 4,969,888 A | 11/1990 | Scholten et al. | |
| 5,000,166 A | 3/1991 | Karpf | |
| 5,011,484 A | 4/1991 | Breard | |
| 5,047,055 A | 9/1991 | Bao et al. | |
| 5,059,193 A | 10/1991 | Kuslich | |
| 5,092,866 A | 3/1992 | Breard et al. | |
| 5,098,433 A | 3/1992 | Freedland | |
| 5,171,278 A | 12/1992 | Pisharodi | |
| 5,171,280 A | 12/1992 | Baumgartner | |
| 5,201,734 A | 4/1993 | Cozad et al. | |
| 5,236,460 A | 8/1993 | Barber | |
| 5,242,444 A | 9/1993 | MacMillan | |
| 5,267,999 A | 12/1993 | Olerud | |
| 5,290,312 A | 3/1994 | Kojimoto et al. | |
| 5,306,275 A | 4/1994 | Bryan | |
| 5,306,310 A | 4/1994 | Siebels | |
| 5,312,405 A | 5/1994 | Korotko et al. | |
| 5,314,477 A | 5/1994 | Marnay | |
| 5,316,422 A | 5/1994 | Coffman | |
| 5,336,264 A * | 8/1994 | Constanz et al. | 424/423 |
| 5,356,423 A | 10/1994 | Tihon et al. | |
| 5,360,430 A | 11/1994 | Lin | |
| 5,366,455 A | 11/1994 | Dove | |
| 5,370,697 A | 12/1994 | Baumgartner | |
| 5,390,683 A | 2/1995 | Pisharodi | |
| 5,395,370 A | 3/1995 | Muller et al. | |
| 5,401,269 A | 3/1995 | Buttner-Janz et al. | |
| 5,403,316 A | 4/1995 | Ashman | |
| 5,415,661 A | 5/1995 | Holmes | |
| 5,437,672 A | 8/1995 | Alleyne | |
| 5,437,674 A | 8/1995 | Worcel et al. | |
| 5,439,463 A | 8/1995 | Lin | |
| 5,454,812 A | 10/1995 | Lin | |
| 5,456,689 A | 10/1995 | Kresch et al. | |
| 5,458,641 A | 10/1995 | Ramirez Jimenez | |
| 5,480,442 A * | 1/1996 | Bertagnoli | 623/17.14 |
| 5,496,318 A | 3/1996 | Howland et al. | |
| 5,518,498 A | 5/1996 | Lindenberg et al. | |
| 5,527,312 A | 6/1996 | Ray | |
| 5,549,679 A | 8/1996 | Kuslich | |
| 5,554,191 A | 9/1996 | Lahille et al. | |
| 5,562,662 A | 10/1996 | Brumfield et al. | |
| 5,562,735 A | 10/1996 | Margulies | |
| 5,562,736 A | 10/1996 | Ray et al. | |
| 5,571,189 A | 11/1996 | Kuslich | |
| 5,571,192 A | 11/1996 | Schonhoffer | |
| 5,609,634 A | 3/1997 | Voydeville | |
| 5,609,635 A | 3/1997 | Michelson | |
| 5,628,756 A | 5/1997 | Barker, Jr. et al. | |
| 5,630,816 A | 5/1997 | Kambin | |
| 5,645,597 A | 7/1997 | Krapiva | |
| 5,645,599 A | 7/1997 | Samani | |
| 5,653,762 A | 8/1997 | Pisharodi | |
| 5,653,763 A | 8/1997 | Errico et al. | |
| 5,658,335 A | 8/1997 | Allen | |
| 5,665,122 A | 9/1997 | Kambin | |
| 5,674,295 A | 10/1997 | Ray et al. | |
| 5,676,702 A | 10/1997 | Ratron | |
| 5,685,826 A | 11/1997 | Bonutti | |
| 5,690,649 A | 11/1997 | Li | |
| 5,693,100 A | 12/1997 | Pisharodi | |
| 5,702,395 A | 12/1997 | Hopf | |
| 5,702,452 A | 12/1997 | Argenson et al. | |
| 5,702,454 A | 12/1997 | Baumgartner | |
| 5,702,455 A | 12/1997 | Saggar | |
| 5,707,390 A | 1/1998 | Bonutti | |
| 5,716,416 A | 2/1998 | Lin | |
| 5,723,013 A * | 3/1998 | Jeanson et al. | 623/17.16 |
| 5,725,341 A | 3/1998 | Hofmeister | |
| 5,725,582 A | 3/1998 | Bevan et al. | |
| 5,746,762 A | 5/1998 | Bass | |
| 5,755,797 A | 5/1998 | Baumgartner | |
| 5,800,547 A | 9/1998 | Schafer et al. | |
| 5,800,549 A | 9/1998 | Bao et al. | |
| 5,810,815 A | 9/1998 | Morales | |
| 5,836,948 A | 11/1998 | Zucherman et al. | |
| 5,849,004 A | 12/1998 | Bramlet | |
| 5,860,977 A * | 1/1999 | Zucherman et al. | 606/249 |
| 5,888,196 A | 3/1999 | Bonutti | |
| 5,941,881 A | 8/1999 | Barnes | |
| 5,964,730 A | 10/1999 | Williams et al. | |
| 5,976,186 A | 11/1999 | Bao et al. | |
| 5,980,523 A | 11/1999 | Jackson | |
| 6,019,792 A | 2/2000 | Cauthen | |
| 6,022,376 A | 2/2000 | Assell et al. | |
| 6,048,342 A | 4/2000 | Zucherman et al. | |
| 6,066,154 A | 5/2000 | Reiley et al. | |
| 6,068,630 A | 5/2000 | Zucherman et al. | |
| 6,074,390 A | 6/2000 | Zucherman et al. | |
| 6,102,922 A | 8/2000 | Jakobsson et al. | |
| 6,126,689 A | 10/2000 | Brett | |
| 6,126,691 A | 10/2000 | Kasra et al. | |
| 6,127,597 A | 10/2000 | Beyar et al. | |
| 6,132,464 A | 10/2000 | Martin | |
| 6,179,874 B1 | 1/2001 | Cauthen | |
| 6,190,413 B1 | 2/2001 | Sutcliffe | |
| 6,190,414 B1 | 2/2001 | Young | |
| 6,214,037 B1 | 4/2001 | Mitchell et al. | |
| 6,214,050 B1 | 4/2001 | Huene | |
| 6,238,397 B1 | 5/2001 | Zucherman et al. | |
| 6,245,107 B1 | 6/2001 | Ferree | |
| 6,277,120 B1 | 8/2001 | Lawson | |
| 6,293,949 B1 | 9/2001 | Justis et al. | |
| 6,299,613 B1 | 10/2001 | Ogilvie et al. | |
| 6,332,894 B1 | 12/2001 | Stalcup et al. | |
| 6,336,930 B1 | 1/2002 | Stalcup et al. | |
| 6,348,053 B1 | 2/2002 | Cachia | |
| 6,352,537 B1 | 3/2002 | Strnad | |
| 6,364,883 B1 | 4/2002 | Santilli | |
| 6,371,987 B1 | 4/2002 | Weiland et al. | |
| 6,375,682 B1 | 4/2002 | Fleischmann et al. | |
| 6,395,034 B1 | 5/2002 | Suddaby | |
| 6,402,750 B1 | 6/2002 | Atkinson et al. | |
| 6,402,751 B1 | 6/2002 | Hoeck et al. | |
| 6,402,785 B1 | 6/2002 | Zdeblick et al. | |
| 6,419,703 B1 | 7/2002 | Fallin et al. | |
| 6,419,704 B1 | 7/2002 | Ferree | |
| 6,425,923 B1 | 7/2002 | Stalcup et al. | |
| 6,432,130 B1 | 8/2002 | Hanson | |
| 6,436,137 B2 * | 8/2002 | Wang et al. | 623/11.11 |
| 6,440,168 B1 | 8/2002 | Cauthen | |
| 6,440,169 B1 | 8/2002 | Elberg et al. | |
| 6,447,513 B1 | 9/2002 | Griggs | |

| Patent No. | Date | Inventor |
|---|---|---|
| 6,447,514 B1 | 9/2002 | Stalcup et al. |
| 6,451,019 B1 | 9/2002 | Zucherman et al. |
| 6,500,178 B2 | 12/2002 | Zucherman et al. |
| 6,511,508 B1 | 1/2003 | Shahinpoor et al. |
| 6,514,256 B2 | 2/2003 | Zucherman et al. |
| 6,520,991 B2 | 2/2003 | Huene |
| 6,554,833 B2 | 4/2003 | Levy |
| 6,558,390 B2 | 5/2003 | Cragg |
| 6,582,433 B2 | 6/2003 | Yun |
| 6,582,467 B1 | 6/2003 | Teitelbaum et al. |
| 6,592,585 B2 | 7/2003 | Lee et al. |
| 6,626,944 B1 | 9/2003 | Taylor |
| 6,645,207 B2 | 11/2003 | Dixon et al. |
| 6,645,248 B2 | 11/2003 | Casutt |
| 6,669,729 B2 | 12/2003 | Chin |
| 6,685,742 B1 | 2/2004 | Jackson |
| 6,695,842 B2 | 2/2004 | Zucherman et al. |
| 6,699,246 B2 | 3/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,531 B1 | 5/2004 | Trieu |
| 6,733,533 B1 | 5/2004 | Lozier |
| 6,733,534 B2 | 5/2004 | Sherman |
| 6,736,818 B2 | 5/2004 | Perren et al. |
| 6,743,257 B2 | 6/2004 | Castro |
| 6,758,863 B2 | 7/2004 | Estes et al. |
| 6,761,720 B1 | 7/2004 | Senegas |
| 6,770,096 B2 | 8/2004 | Bolger et al. |
| 6,783,530 B1 | 8/2004 | Levy |
| 6,805,697 B1 | 10/2004 | Helm et al. |
| 6,835,205 B2 | 12/2004 | Atkinson et al. |
| 6,852,128 B2 | 2/2005 | Lange |
| 6,863,688 B2 | 3/2005 | Ralph et al. |
| 6,899,713 B2 | 5/2005 | Shaolian et al. |
| 6,902,580 B2 | 6/2005 | Fallin et al. |
| 6,905,512 B2 | 6/2005 | Paes et al. |
| 6,946,000 B2 | 9/2005 | Senegas et al. |
| 6,958,077 B2 | 10/2005 | Suddaby |
| 6,969,404 B2 | 11/2005 | Ferree |
| 6,969,405 B2 | 11/2005 | Suddaby |
| 6,972,036 B2 | 12/2005 | Boehm, Jr. et al. |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,070,598 B2 | 7/2006 | Lim et al. |
| 7,081,120 B2 | 7/2006 | Li et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,097,654 B1 | 8/2006 | Freedland |
| 7,101,375 B2 | 9/2006 | Zucherman et al. |
| 7,105,024 B2 | 9/2006 | Richelsoph |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,431,735 B2 | 10/2008 | Liu et al. |
| 7,442,208 B2 | 10/2008 | Mathieu et al. |
| 7,442,210 B2 | 10/2008 | Segal et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 7,621,950 B1 | 11/2009 | Globerman et al. |
| 7,658,752 B2 | 2/2010 | Labrom et al. |
| 7,749,252 B2 | 7/2010 | Zucherman et al. |
| 7,771,456 B2 | 8/2010 | Hartman et al. |
| 7,862,615 B2 | 1/2011 | Carli et al. |
| 7,901,430 B2 | 3/2011 | Matsuura et al. |
| 2001/0016743 A1 | 8/2001 | Zucherman et al. |
| 2002/0029039 A1* | 3/2002 | Zucherman et al. ............ 606/61 |
| 2002/0082600 A1 | 6/2002 | Shaolian et al. |
| 2002/0133155 A1 | 9/2002 | Ferree |
| 2002/0143331 A1 | 10/2002 | Zucherman et al. |
| 2002/0147449 A1* | 10/2002 | Yun ................................ 606/61 |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0139814 A1 | 7/2003 | Bryan |
| 2003/0153915 A1 | 8/2003 | Nekozuka et al. |
| 2003/0220649 A1 | 11/2003 | Bao et al. |
| 2004/0010312 A1 | 1/2004 | Enayati |
| 2004/0010316 A1 | 1/2004 | William et al. |
| 2004/0055607 A1 | 3/2004 | Boehm, Jr. et al. |
| 2004/0083002 A1 | 4/2004 | Belef et al. |
| 2004/0087947 A1 | 5/2004 | Lim et al. |
| 2004/0097931 A1 | 5/2004 | Mitchell |
| 2004/0106995 A1 | 6/2004 | LeCouedic et al. |
| 2004/0117017 A1 | 6/2004 | Pasquet et al. |
| 2004/0133204 A1 | 7/2004 | Davies |
| 2004/0133280 A1 | 7/2004 | Trieu |
| 2004/0158248 A1 | 8/2004 | Ginn |
| 2004/0167625 A1 | 8/2004 | Beyar et al. |
| 2004/0186475 A1 | 9/2004 | Falahee |
| 2004/0186576 A1 | 9/2004 | Biscup et al. |
| 2004/0199255 A1 | 10/2004 | Mathieu et al. |
| 2004/0215342 A1 | 10/2004 | Suddaby |
| 2004/0225360 A1 | 11/2004 | Malone |
| 2004/0230305 A1 | 11/2004 | Gorensek et al. |
| 2004/0260397 A1 | 12/2004 | Lambrecht et al. |
| 2005/0010293 A1 | 1/2005 | Zucherman et al. |
| 2005/0015140 A1* | 1/2005 | deBeer ........................ 623/1.21 |
| 2005/0033431 A1 | 2/2005 | Gordon et al. |
| 2005/0033432 A1 | 2/2005 | Gordon et al. |
| 2005/0033434 A1 | 2/2005 | Berry |
| 2005/0033437 A1 | 2/2005 | Bao et al. |
| 2005/0033439 A1 | 2/2005 | Gordon et al. |
| 2005/0038432 A1 | 2/2005 | Shaolian et al. |
| 2005/0049708 A1 | 3/2005 | Atkinson et al. |
| 2005/0085814 A1 | 4/2005 | Sherman et al. |
| 2005/0101955 A1 | 5/2005 | Zucherman et al. |
| 2005/0143738 A1 | 6/2005 | Zucherman et al. |
| 2005/0143827 A1 | 6/2005 | Globerman et al. |
| 2005/0165398 A1 | 7/2005 | Reiley |
| 2005/0197702 A1 | 9/2005 | Coppes et al. |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0203626 A1 | 9/2005 | Sears et al. |
| 2005/0209696 A1 | 9/2005 | Lin et al. |
| 2005/0216017 A1 | 9/2005 | Fielding et al. |
| 2005/0228391 A1 | 10/2005 | Levy et al. |
| 2005/0240267 A1 | 10/2005 | Randall et al. |
| 2005/0245937 A1 | 11/2005 | Winslow |
| 2005/0261768 A1 | 11/2005 | Trieu |
| 2005/0267579 A1 | 12/2005 | Reiley et al. |
| 2005/0267580 A1 | 12/2005 | Suddaby |
| 2005/0273110 A1 | 12/2005 | Boehm, Jr. et al. |
| 2005/0273166 A1 | 12/2005 | Sweeney |
| 2005/0288672 A1 | 12/2005 | Feree |
| 2006/0004367 A1 | 1/2006 | Alamin et al. |
| 2006/0004447 A1* | 1/2006 | Mastrorio et al. ......... 623/17.11 |
| 2006/0004455 A1 | 1/2006 | Leonard et al. |
| 2006/0015181 A1 | 1/2006 | Elberg |
| 2006/0015183 A1 | 1/2006 | Gilbert et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0058790 A1 | 3/2006 | Carl et al. |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |

| | | |
|---|---|---|
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 | 6/2006 | Taylor |
| 2006/0142858 A1 | 6/2006 | Colleran et al. |
| 2006/0149242 A1 | 7/2006 | Kraus et al. |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0224241 A1 | 10/2006 | Butler et al. |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Brueneau et al. |
| 2006/0241643 A1 | 10/2006 | Lim et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0271061 A1 | 11/2006 | Beyar et al. |
| 2006/0282075 A1 | 12/2006 | Labrom et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0010813 A1 | 1/2007 | Zucherman et al. |
| 2007/0032790 A1 | 2/2007 | Aschmann et al. |
| 2007/0043362 A1 | 2/2007 | Malandain et al. |
| 2007/0043363 A1 | 2/2007 | Malandain et al. |
| 2007/0073289 A1 | 3/2007 | Kwak et al. |
| 2007/0088436 A1 | 4/2007 | Parsons et al. |
| 2007/0100340 A1 | 5/2007 | Lange et al. |
| 2007/0123861 A1 | 5/2007 | Dewey et al. |
| 2007/0142915 A1 | 6/2007 | Altarac et al. |
| 2007/0151116 A1 | 7/2007 | Malandain |
| 2007/0162000 A1 | 7/2007 | Perkins |
| 2007/0162136 A1 | 7/2007 | O'Neil et al. |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0198091 A1 | 8/2007 | Boyer et al. |
| 2007/0225807 A1 | 9/2007 | Phan et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0282443 A1 | 12/2007 | Globerman et al. |
| 2008/0021457 A1 | 1/2008 | Anderson et al. |
| 2008/0021460 A1 | 1/2008 | Bruneau et al. |
| 2008/0058934 A1 | 3/2008 | Malandain et al. |
| 2008/0097446 A1 | 4/2008 | Reiley et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0183209 A1 | 7/2008 | Robinson et al. |
| 2008/0183211 A1 | 7/2008 | Lamborne et al. |
| 2008/0183218 A1 | 7/2008 | Mueller et al. |
| 2008/0195152 A1 | 8/2008 | Altarac et al. |
| 2008/0215094 A1 | 9/2008 | Taylor |
| 2008/0221685 A9 | 9/2008 | Altarac et al. |
| 2008/0234824 A1 | 9/2008 | Youssef et al. |
| 2008/0262617 A1 | 10/2008 | Froehlich et al. |
| 2008/0281360 A1 | 11/2008 | Vittur et al. |
| 2008/0281361 A1 | 11/2008 | Vittur et al. |
| 2009/0062915 A1 | 3/2009 | Kohm et al. |
| 2009/0105766 A1 | 4/2009 | Thompson et al. |
| 2009/0105773 A1 | 4/2009 | Lange et al. |
| 2009/0234389 A1 | 9/2009 | Chuang et al. |
| 2009/0240283 A1 | 9/2009 | Carls et al. |
| 2009/0270918 A1 | 10/2009 | Attia et al. |
| 2010/0121379 A1 | 5/2010 | Edmond |
| 2010/0204732 A1 | 8/2010 | Aschmann et al. |

FOREIGN PATENT DOCUMENTS

| | | |
|---|---|---|
| DE | 3922044 A1 | 2/1991 |
| DE | 4012622 C1 | 7/1991 |
| DE | 101 49 385 A1 | 4/2003 |
| EP | 0418387 A1 | 3/1991 |
| EP | 0322334 B1 | 2/1992 |
| EP | 0 661 957 B1 | 9/1998 |
| EP | 0767636 B1 | 1/1999 |
| EP | 1004276 A1 | 5/2000 |
| EP | 1011464 B1 | 6/2000 |
| EP | 1138268 A1 | 10/2001 |
| EP | 1148850 B1 | 10/2001 |
| EP | 1148851 B1 | 10/2001 |
| EP | 1302169 A1 | 4/2003 |
| EP | 1330987 A1 | 7/2003 |
| EP | 1552797 A2 | 7/2005 |
| EP | 1854433 A1 | 11/2007 |
| EP | 1905392 A1 | 4/2008 |
| EP | 1982664 A1 | 10/2008 |
| FR | 2623085 A1 | 5/1989 |
| FR | 2625097 A1 | 6/1989 |
| FR | 2681525 A | 3/1993 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A | 1/1996 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799640 A | 4/2001 |
| FR | 2799948 A1 | 4/2001 |
| FR | 2816197 A1 | 5/2002 |
| FR | 2851154 A | 8/2004 |
| JP | 02-224660 | 9/1990 |
| JP | 09-075381 | 3/1997 |
| JP | 2003079649 | 3/2003 |
| SU | 988281 | 1/1983 |
| SU | 1484348 | 6/1989 |
| SU | 1484348 A1 | 6/1989 |
| WO | WO 91/13598 | 9/1991 |
| WO | WO 94/26192 | 11/1994 |
| WO | WO 94/26195 | 11/1994 |
| WO | 97/18769 | 5/1997 |
| WO | WO 98/20939 | 5/1998 |
| WO | WO 98/34568 | 8/1998 |
| WO | WO 99/26562 | 6/1999 |
| WO | WO 99/59669 | 11/1999 |

| | | |
|---|---|---|
| WO | WO 00/44319 | 8/2000 |
| WO | WO 00/45752 | 8/2000 |
| WO | WO 01/15638 A1 | 3/2001 |
| WO | WO 01/54598 A1 | 8/2001 |
| WO | WO 02/09625 A1 | 2/2002 |
| WO | WO 03/007829 | 1/2003 |
| WO | WO 03/057055 A1 | 7/2003 |
| WO | WO 2004/028401 A2 | 4/2004 |
| WO | WO 2004/047689 A1 | 6/2004 |
| WO | WO 2004/047691 A1 | 6/2004 |
| WO | 2006/089085 A | 8/2004 |
| WO | 2004/084743 A1 | 10/2004 |
| WO | 2004/084768 A | 10/2004 |
| WO | WO 2004/084768 A2 | 10/2004 |
| WO | 2004/110300 A2 | 12/2004 |
| WO | 2005/002474 A | 1/2005 |
| WO | WO 2005/002474 A1 | 1/2005 |
| WO | 2005/009300 A | 2/2005 |
| WO | WO 2005/009300 A1 | 2/2005 |
| WO | WO 2005/011507 A1 | 2/2005 |
| WO | WO 2005/016194 A2 | 2/2005 |
| WO | WO 2005/044118 A1 | 5/2005 |
| WO | WO 2005/048856 A1 | 6/2005 |
| WO | WO 2005/097004 A2 | 10/2005 |
| WO | WO 2005/110258 A1 | 11/2005 |
| WO | WO 2005/115261 A1 | 12/2005 |
| WO | WO 2006/009855 A2 | 1/2006 |
| WO | 2006/025815 A | 3/2006 |
| WO | 2006/044786 A | 4/2006 |
| WO | WO 2006/064356 A1 | 6/2006 |
| WO | WO 2007/034516 A1 | 3/2007 |
| WO | WO 2007052975 A1 | 5/2007 |
| WO | 2007/075788 A | 7/2007 |
| WO | 2009/083276 A1 | 7/2009 |
| WO | 2009/083583 A1 | 7/2009 |
| WO | 2009/098536 A1 | 8/2009 |

OTHER PUBLICATIONS

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

DuBois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Duff, "Methyl Methacrylate in Spinal Stabilization," Techniques in Spinal Fusion and Stabilization, Hitchon et al., eds., 1995, pp. 147-151, Ch. 14, Thieme, New York.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

Anasetti et al., "Spine Stability After Implantation Of An Interspinous Device: An In Vitro And Finite Element Biomechanical Study," J. Neurosurg. Spine, Nov. 2010, vol. 13, pp. 568-575.

Bellini et al., "Biomechanics Of the Lumbar Spine Afer Dynamic Stabilization," J. Spinal Discord Tech., 2006, vol. 00, No. 00, pp. 1-7.

Buric et al., "DIAM Device For Low Back Pain In Degenerative Disc Disease 24 Months Follow-up," Advances in Minimally Invasive Surgery And Therapy For Spine And Nerves, Alexandre et al., eds., 2011, pp. 177-182, Spinger-Verlat/Wien.

Phillips et al., "Biomechanics Of Posterior Dynamic Stabiling Device (DIAM) After Facetectomy And Disectomy," The Spine Journal, 2006, vol. 6, pp. 714-722.

Taylor et al., "Device For Intervertebral Assisted Motion: Technique and Intial Results," 22 Neurosurg. Focus, Jan. 2007, vol. 22, No. 1, pp. 1-6.

Wilke et al., "Biomedical Effect Of Different Lumbar Interspinous Implants On Flexibilty And Intradiscal Pressure," Eur Spine J., Vo. 17, published online Jun. 27, 2008, pp. 1049-1056.

Zhao et al., "Efficacy Of The Dynamic Interspinous Assisted Motion System In Clinical Treatment Of Degenerative Lumbar Disease," Chin. Med. J., 2010, vol. 123, No. 21, pp. 2974-2977.

* cited by examiner

US 8,048,118 B2

ADJUSTABLE INTERSPINOUS PROCESS BRACE

FIELD OF THE DISCLOSURE

The present disclosure relates generally to orthopedics and orthopedic surgery. More specifically, the present disclosure relates to devices used to support adjacent spinous processes.

BACKGROUND

In human anatomy, the spine is a generally flexible column that can take tensile and compressive loads. The spine also allows bending motion and provides a place of attachment for keels, muscles and ligaments. Generally, the spine is divided into three sections: the cervical spine, the thoracic spine and the lumbar spine. The sections of the spine are made up of individual bones called vertebrae. Also, the vertebrae are separated by intervertebral discs, which are situated between adjacent vertebrae.

The intervertebral discs function as shock absorbers and as joints. Further, the intervertebral discs can absorb the compressive and tensile loads to which the spinal column may be subjected. At the same time, the intervertebral discs can allow adjacent vertebral bodies to move relative to each other a limited amount, particularly during bending, or flexure, of the spine. Thus, the intervertebral discs are under constant muscular and/or gravitational pressure and generally, the intervertebral discs are the first parts of the lumbar spine to show signs of deterioration.

Facet joint degeneration is also common because the facet joints are in almost constant motion with the spine. In fact, facet joint degeneration and disc degeneration frequently occur together. Generally, although one may be the primary problem while the other is a secondary problem resulting from the altered mechanics of the spine, by the time surgical options are considered, both facet joint degeneration and disc degeneration typically have occurred. For example, the altered mechanics of the facet joints and/or intervertebral disc may cause spinal stenosis, degenerative spondylolisthesis, and degenerative scoliosis.

DETAILED DESCRIPTION OF THE DRAWINGS

Figure 1:
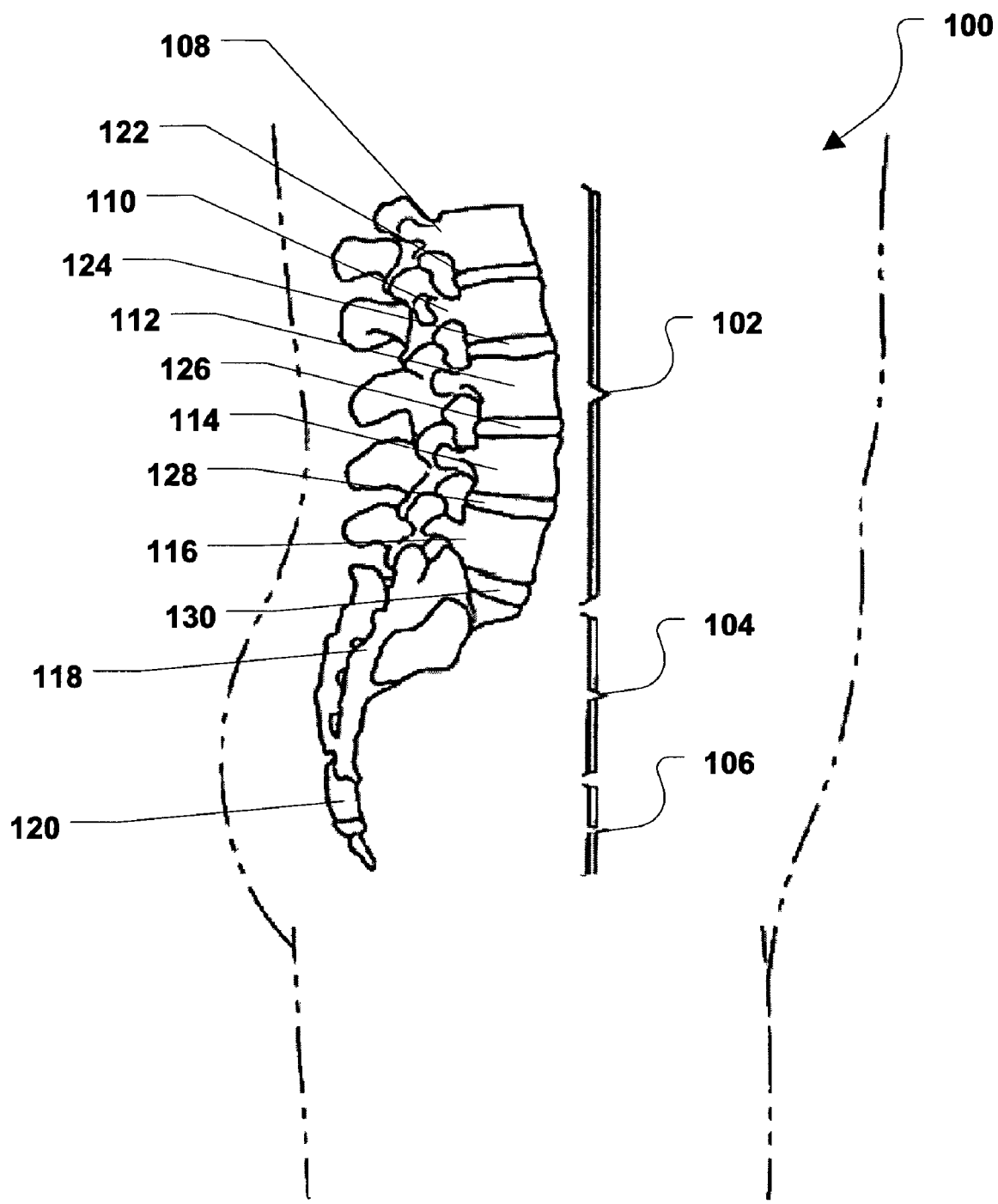
FIG. 1 is a lateral view of a portion of a vertebral column.

An adjustable interspinous process brace is disclosed and can include a superior component. The superior component can include a superior spinous process bracket that can engage a superior spinous process. Further, the adjustable interspinous process brace can include an inferior component. The inferior component can include an inferior spinous process bracket that can engage an inferior spinous process. Further, the inferior component can be movably engaged with the superior component from a retracted position to an extended position. In the extended position, a distance between the superior spinous process bracket and the inferior spinous process bracket can be increased.

In another embodiment, an adjustable interspinous process brace is disclosed and can include a superior spinous process bracket that can engage a superior spinous process. Also, the adjustable interspinous process brace can include an inferior spinous process bracket that can engage an inferior spinous process. The inferior spinous process bracket can move relative to the superior spinous process bracket from a first position to a second position.

In yet another embodiment, a method of treating a spine is disclosed and can include distracting a superior vertebra and an inferior vertebra. Moreover, the method can include installing an adjustable interspinous process brace between a superior spinous process and an inferior spinous process and adjusting the adjustable interspinous process brace to support the superior spinous process and the inferior spinous process.

In still another embodiment, a method of treating a spine is disclosed and can include installing an adjustable interspinous process brace between a superior spinous process and an inferior spinous process. Further, the method can include injecting an injectable biocompatible material into the adjustable interspinous process brace to increase a distance between the superior spinous process and the inferior spinous process.

In yet still another embodiment, an adjustable interspinous process brace is disclosed and can include a superior component. The superior component can include a superior bracket that can engage a portion of a superior vertebra. Additionally, the adjustable interspinous process brace can include an inferior component and the inferior component can include an inferior bracket that can engage a portion of an inferior vertebra. The inferior component can be movably engaged with the superior component from a retracted position to an extended position in which a distance between the superior bracket and the inferior bracket can be increased.

In another embodiment, a kit for field use is disclosed and includes an adjustable interspinous process brace that can have an interior chamber that can receive an injectable biocompatible material. The kit can also include an injectable biocompatible material.

In still another embodiment, a kit for field use is disclosed and can include an adjustable interspinous process brace that can have an interior chamber that can receive a spacer. Further, the kit can include a plurality of spacers.

Description of Relevant Anatomy

Referring initially to FIG. 1, a portion of a vertebral column, designated 100, is shown. As depicted, the vertebral column 100 includes a lumbar region 102, a sacral region 104, and a coccygeal region 106. As is known in the art, the vertebral column 100 also includes a cervical region and a thoracic region. For clarity and ease of discussion, the cervical region and the thoracic region are not illustrated.

As shown in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114. Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

In a particular embodiment, if one of the intervertebral lumbar discs 122, 124, 126, 128, 130 is diseased, degenerated, damaged, or otherwise in need of repair, treatment of that intervertebral lumbar disc 122, 124, 126, 128, 130 can be effected in accordance with one or more of the embodiments described herein.

Figure 2:
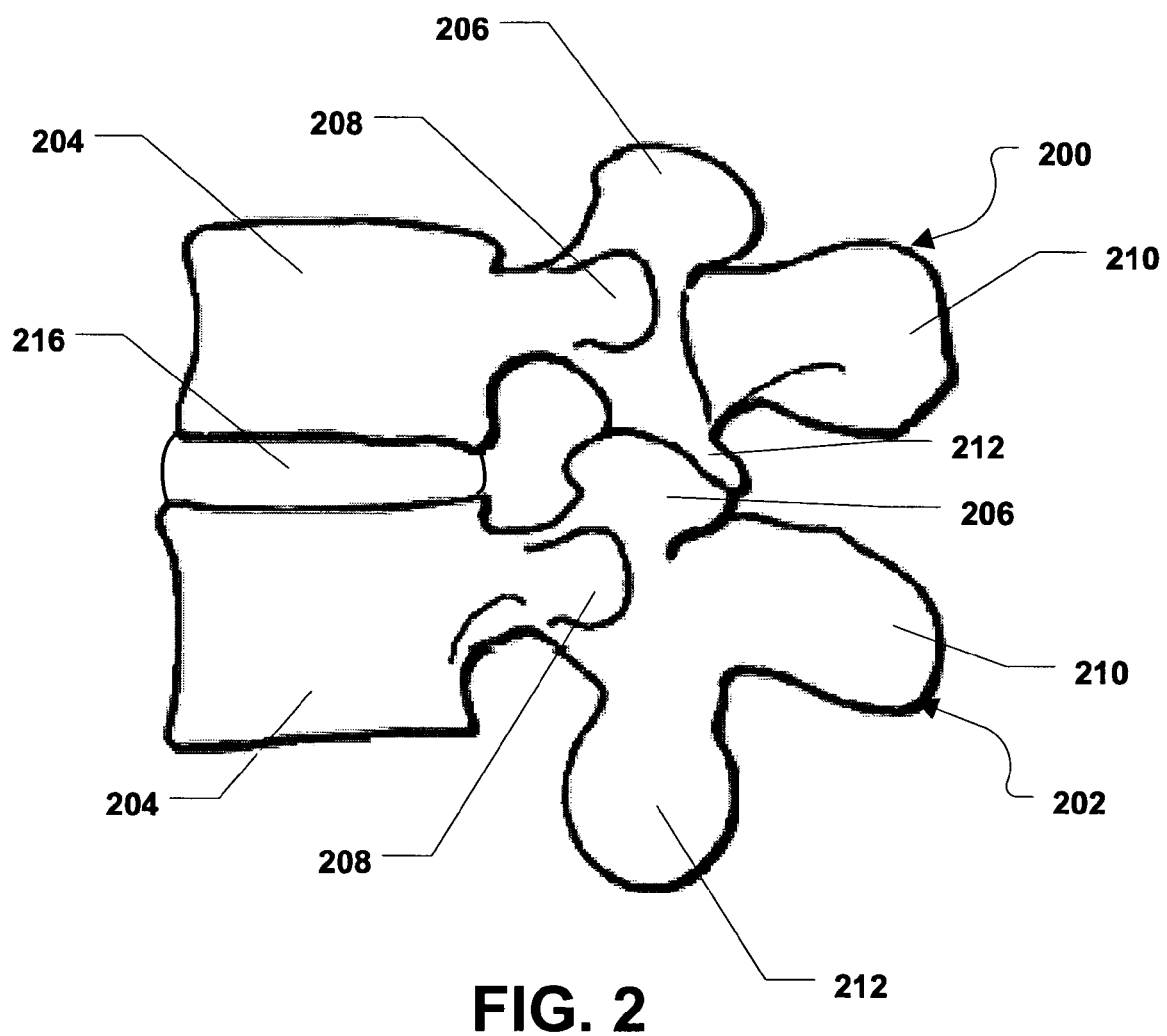
FIG. 2 is a lateral view of a pair of adjacent vertebrae.

FIG. 2 depicts a detailed lateral view of two adjacent vertebrae, e.g., two of the lumbar vertebra 108, 110, 112, 114, 116 shown in FIG. 1. FIG. 2 illustrates a superior vertebra 200 and an inferior vertebra 202. As shown, each vertebra 200, 202 includes a vertebral body 204, a superior articular process 206, a transverse process 208, a spinous process 210 and an inferior articular process 212. FIG. 2 further depicts an intervertebral disc 216 between the superior vertebra 200 and the inferior vertebra 202.

Figure 3:
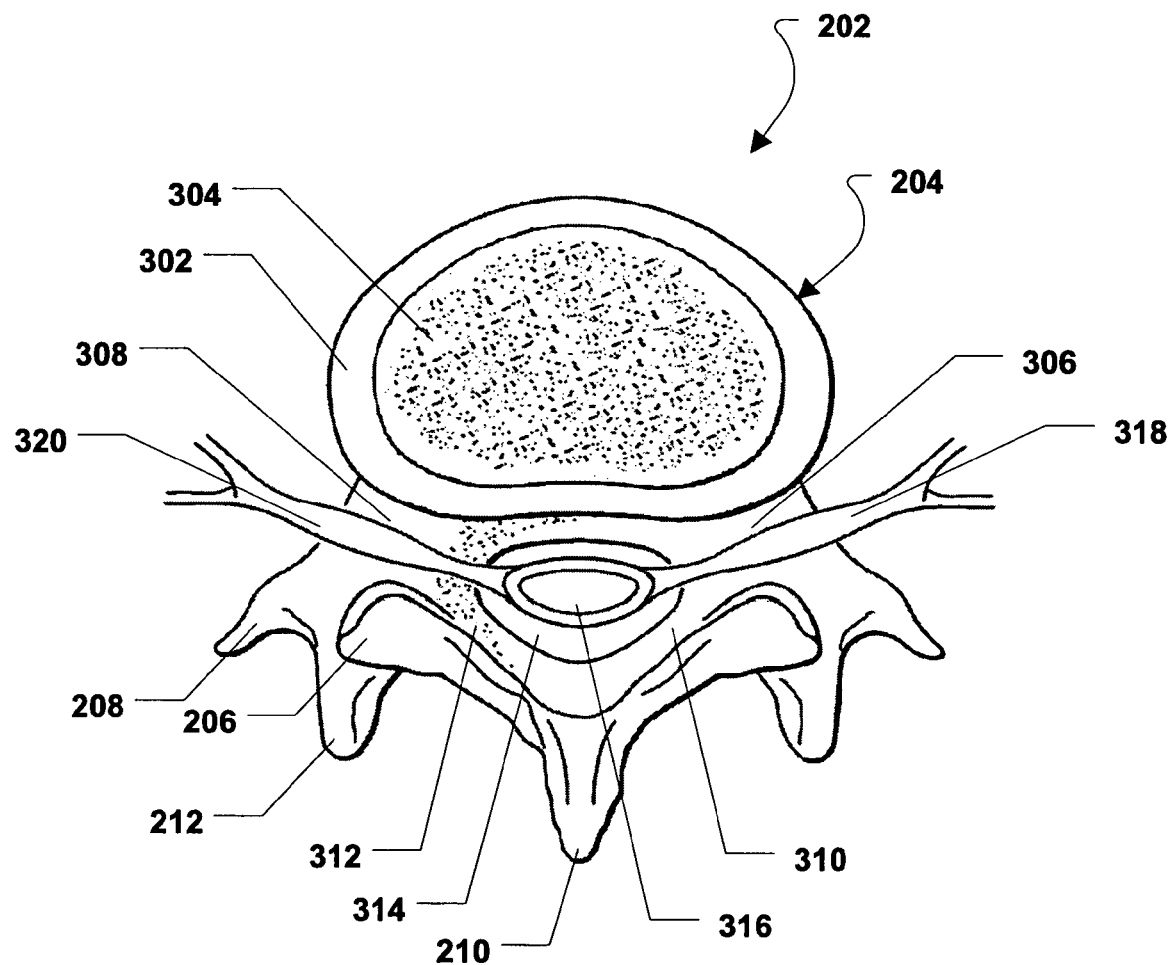
FIG. 3 is a top plan view of a vertebra.

Referring to FIG. 3, a vertebra, e.g., the inferior vertebra 202 (FIG. 2), is illustrated. As shown, the vertebral body 204 of the inferior vertebra 202 includes a cortical rim 302 composed of cortical bone. Also, the vertebral body 204 includes cancellous bone 304 within the cortical rim 302. The cortical rim 302 is often referred to as the apophyseal rim or apophyseal ring. Further, the cancellous bone 304 is softer than the cortical bone of the cortical rim 302.

As illustrated in FIG. 3, the inferior vertebra 202 further includes a first pedicle 306, a second pedicle 308, a first lamina 310, and a second lamina 312. Further, a vertebral foramen 314 is established within the inferior vertebra 202. A spinal cord 316 passes through the vertebral foramen 314. Moreover, a first nerve root 318 and a second nerve root 320 extend from the spinal cord 316.

It is well known in the art that the vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2 and FIG. 3. The first and second cervical vertebrae are structurally different than the rest of the vertebrae in order to support a skull.

Description of a First Embodiment of an Adjustable Interspinous Process Brace

Figure 4:
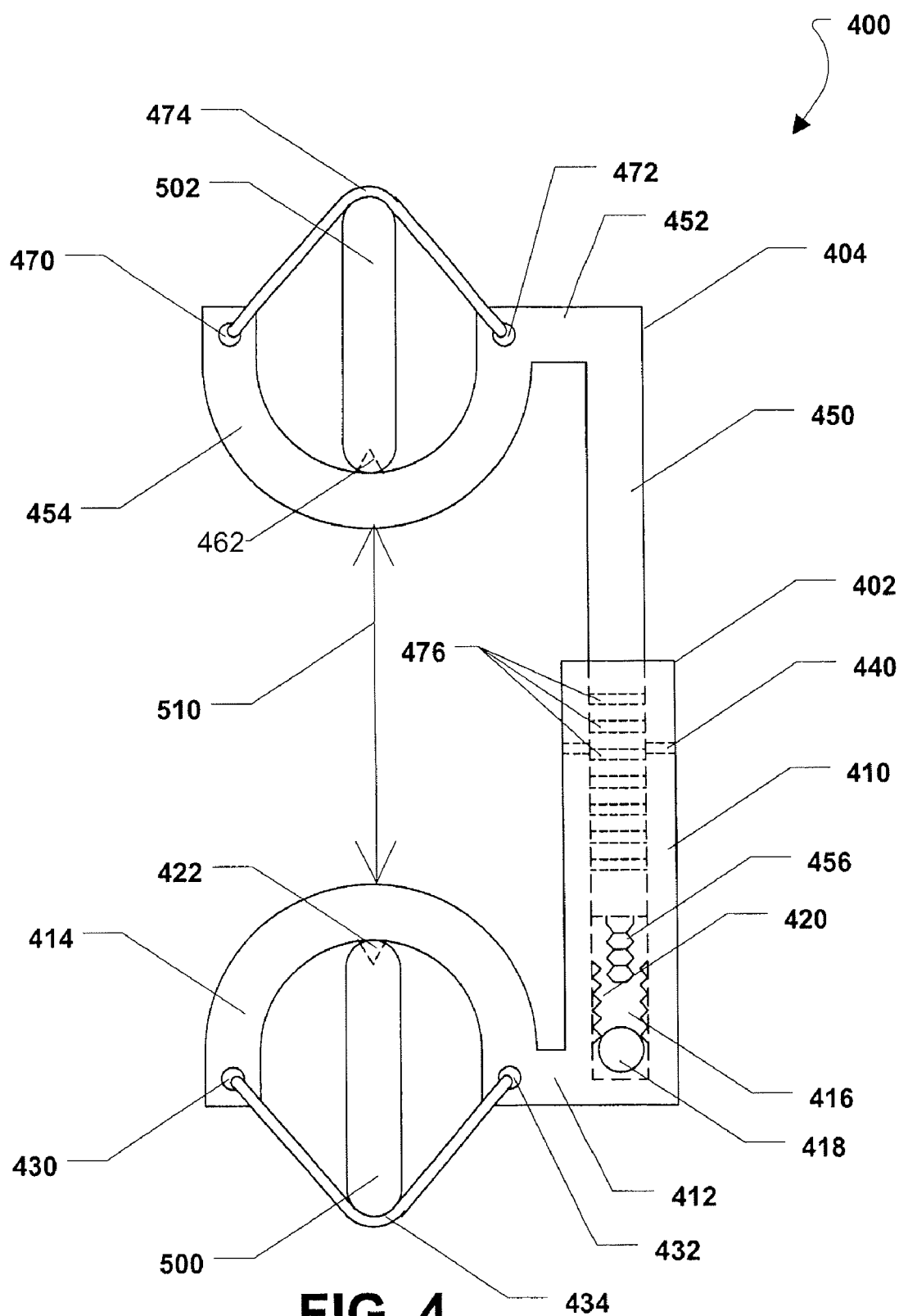
FIG. 4 is a plan view of a first adjustable interspinous process spacer in a retracted position.
Figure 5:
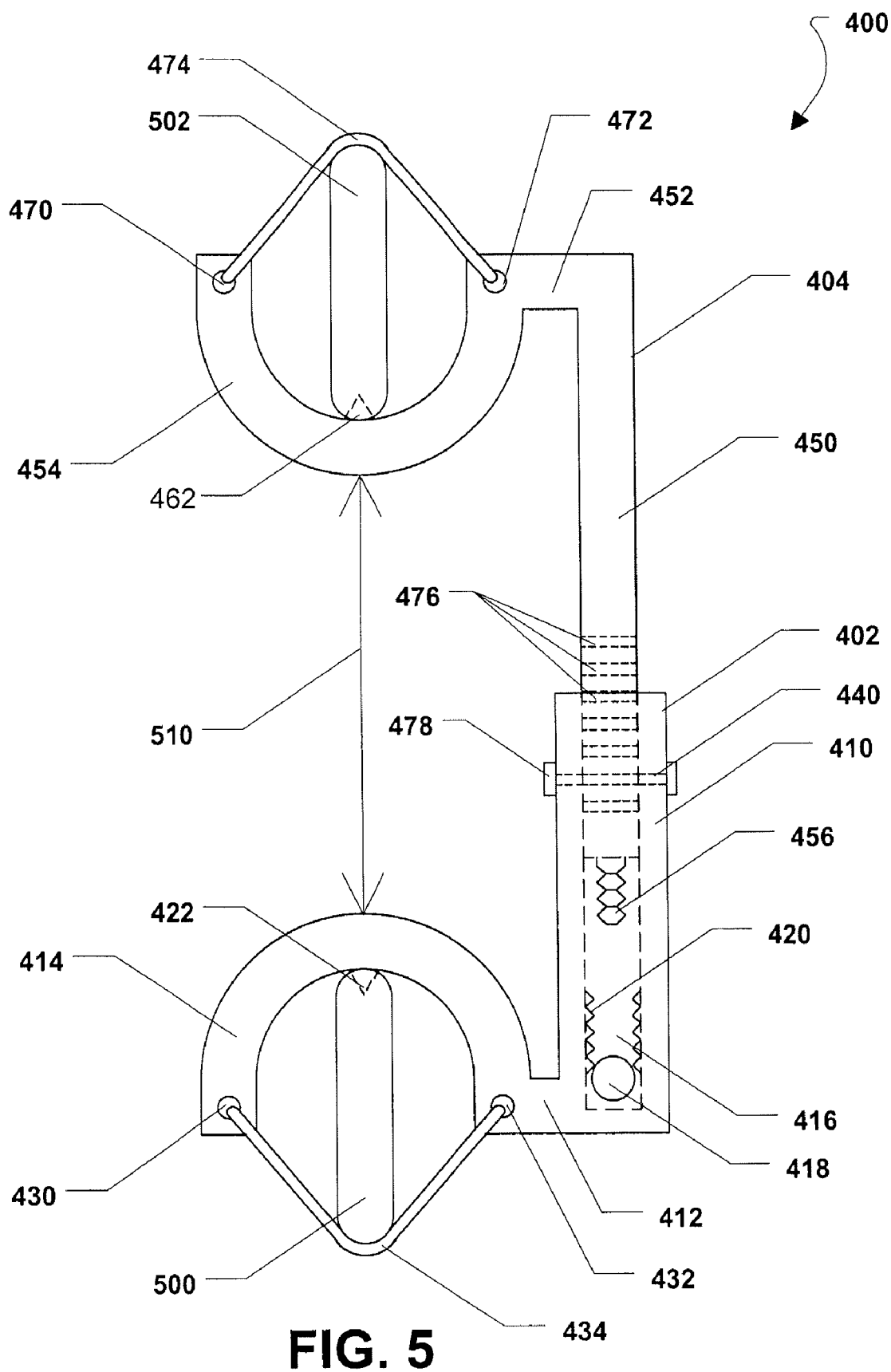
FIG. 5 is a plan view of the first adjustable interspinous process spacer in an extended position.

Referring to FIG. 4 and FIG. 5, a first adjustable interspinous process brace is shown and is generally designated 400. As shown, the adjustable interspinous process brace 400 includes an inferior component 402 and a superior component 404. In a particular embodiment, the components 402, 404 can be made from one or more biocompatible materials. For example, the materials can be metal containing materials, polymer materials, or composite materials that include metals, polymers, or combinations of metals and polymers.

In a particular embodiment, the metal containing materials can be metals. Further, the metal containing materials can be ceramics. Also, the metals can be pure metals or metal alloys. The pure metals can include titanium. Moreover, the metal alloys can include stainless steel, a cobalt-chrome-molybdenum alloy, e.g., ASTM F-999 or ASTM F-75, a titanium alloy, or a combination thereof.

The polymer materials can include polyurethane materials, polyolefin materials, polyaryletherketone (PAEK) materials, silicone materials, hydrogel materials, or a combination thereof. Further, the polyolefin materials can include polypropylene, polyethylene, halogenated polyolefin, flouropolyolefin, or a combination thereof. The polyaryletherketon (PAEK) materials can include polyetherketone (PEK), polyetheretherketone (PEEK), polyetherketoneketone (PEKK), polyetherketoneetherketoneketone (PEKEKK), or a combination thereof. The hydrogels can include polyacrylamide, poly-N-isopropylacrylamine, polyvinyl methylether, polyvinyl alcohol, polyethyl hydroxyethyl cellulose, poly(2-ethyl)oxazoline, polyethyleneoxide, polyethylglycol, polyethylene glycol, polyacrylic acid, polyacrylonitrile, polyvinylacrylate, polyvinylpyrrolidone, or a combination thereof. Alternatively, the components 402, 404 can be made from any other substantially rigid biocompatible materials.

As illustrated in FIG. 4 and FIG. 5, the inferior component 402 can include an inferior support post 410. An inferior lateral arm 412 can extend from the inferior support post 410. Further, an inferior spinous process bracket 414 can extend from the inferior lateral arm 412.

In a particular embodiment, the inferior support post 410 can be hollow and can include an interior chamber 416. Moreover, a lateral cross-section of the inferior support post 410 can indicate that the inferior support post 410 can be generally cylindrical. Alternatively, the inferior support post 410 can have a cross-section that is generally prismatic. Moreover, the inferior support post 410 can have any generally polyhedral shape with a central opening, or interior chamber, formed therein. Also, the inferior support post 410 can include an injection port 418 established therein. In a particular embodiment, the injection port 418 can lead to the interior chamber 416 and can be used to facilitate injection of a material into the interior chamber 416 within the inferior support post 410.

FIG. 4 and FIG. 5 show that the interior chamber 416 within the inferior support post 410 can include one or more corrugations 420. After a material is injected into the interior chamber 416 and cured, the corrugations 420 can substantially prevent relative motion between the cured material and the interior chamber 416.

As indicated in FIG. 4 and FIG. 5, the inferior spinous process bracket 414 can be generally U shaped. Alternatively, the inferior spinous process bracket 414 can be generally V shaped. Further, the inferior spinous process bracket 414 can include an inferior spinous process engagement structure 422 that extends from the inferior spinous process bracket 414. In a particular embodiment, the inferior spinous process engagement structure 422 can be one or more spikes, one or more teeth, a combination thereof, or some other structure configured to engage a spinous process.

The inferior component 402 can also include a first inferior tether hole 430 and a second inferior tether hole 432. An inferior tether 434 can span the inferior component 402, e.g., between the first inferior tether hole 430 and the second inferior tether hole 432. Further, the inferior tether 434 can be looped at least partially around a spinous process and can substantially maintain the spinous process in contact with the inferior spinous process bracket 414. In a particular embodiment, the inferior tether 434 can comprise a biocompatible elastomeric material that flexes during installation and provides a resistance fit against the inferior process. Further, the inferior tether 434 can comprise a substantially non-resorbable suture or the like.

FIG. 4 and FIG. 5 also show that the inferior component 402 can include a hole 440 through the inferior support post 410. The hole 440 is configured to receive a locking pin, described below.

As illustrated in FIG. 4 and FIG. 5, the superior component 404 can include a superior support post 450. A superior lateral arm 452 can extend from the superior support post 450. Further, a superior spinous process bracket 454 can extend from the superior lateral arm 452.

In a particular embodiment, the superior support post 450 can be sized and shaped to fit into the inferior support post 410. Moreover, a lateral cross-section of the superior support post 450 can indicate that the superior support post 450 can be solid and generally cylindrical. Alternatively, the superior support post 450 can have a cross-section that is generally prismatic. Further, the superior support post 450 can have any generally polyhedral shape.

FIG. 4 and FIG. 5 indicate that the superior support post 450 can include a corrugated tip 456. After a material is injected into the interior chamber 416 within the inferior support post 410 and cured, the corrugated tip 456 can substantially prevent relative motion between the superior support post 450 and the cured material. Accordingly, the corrugated tip 456 and the corrugations 420 formed within the interior chamber 416 can substantially prevent the superior support post 450 from being withdrawn, or otherwise pulled, from the interior chamber 416 within the inferior support post 410.

As indicated in FIG. 4 and FIG. 5, the superior spinous process bracket 454 can be generally U shaped. Alternatively, the superior spinous process bracket 454 can be generally V shaped. Further, the superior spinous process bracket 454 can include a superior spinous process engagement structure 462 that extends from the superior spinous process bracket 454. In a particular embodiment, the superior spinous process engagement structure 462 can be one or more spikes, one or more teeth, a combination thereof, or some other structure configured to engage a spinous process.

The superior component 404 can also include a first superior tether hole 470 and a second superior tether hole 472. A superior tether 474 can span the superior component 404, e.g., between the first superior tether hole 470 and the second superior tether hole 472. Further, the superior tether 474 can be looped at least partially around a spinous process and can substantially maintain the spinous process in contact with the superior spinous process bracket 454. In a particular embodiment, the superior tether 474 can comprise a biocompatible elastomeric material that flexes during installation and provides a resistance fit against the inferior process. Further, the superior tether 474 can comprise a substantially non-resorbable suture or the like. FIG. 4 and FIG. 5 also show that the superior component 404 can include a plurality of holes 476 through the superior support post 450.

In a particular embodiment, one of the holes 476 in the superior support post 450 can be aligned with the hole 440 in the inferior support post 410 and a locking pin 478 can be inserted there through in order to substantially prevent any movement between the inferior component 402 and the superior component 404. Accordingly, the adjustable interspinous process brace 400 can be locked in order to substantially resist compressive and tensile loads.

In a particular embodiment, when the adjustable interspinous process brace 400 is properly installed between a superior vertebra and an inferior vertebra, the inferior spinous process bracket 414 can engage and support an inferior spinous process 500. Further, the superior spinous process bracket 454 can engage and support a superior spinous process 502. More specifically, the inferior spinous process engagement structure 422 can extend slightly into and engage the inferior spinous process 500. Also, the superior spinous process engagement structure 462 can extend slightly into and engage the superior spinous process 502. Accordingly, the spinous process engagement structures 422, 462 and the tethers 434, 474 can substantially prevent the adjustable interspinous process brace 400 from migrating with respect to the spinous processes 500, 502.

Also, in a particular embodiment, the adjustable interspinous process brace 400 can be movable between a retracted position, shown in FIG. 4, and one or more extended positions, shown in FIG. 5. In the retracted position, a distance 510 between the inferior spinous process bracket 414 and the superior spinous process bracket 454 can be at a minimum. However, when a material is injected into the interior chamber 416 within the inferior support post 410, the distance 510 between the inferior spinous process bracket 414 and the superior spinous process bracket 454 can be greater than when in the retracted position.

Accordingly, the adjustable interspinous process brace 400 can be installed between an inferior spinous process 500 and a superior spinous process 502. Further, the superior component 404 can be moved relative to the inferior component 402, e.g., by injecting material into the interior chamber 416 within the inferior support post 410, in order to increase the distance between the superior spinous process 502 and the inferior spinous process 500.

Alternatively, a distractor can be used to increase the distance between the superior spinous process 502 and the inferior spinous process 500 and the adjustable interspinous process brace 400 can be adjusted to support the superior spinous process 502 and the inferior spinous process 500. After the adjustable interspinous process brace 400 is adjusted accordingly, the distractor can be removed and the adjustable interspinous process brace 400 can support the superior spinous process 502 and the inferior spinous process 500 to substantially prevent the distance between the superior spinous process 502 and the inferior spinous process 500 from returning to a pre-distraction value. Further, the adjustable interspinous process brace 400 can dynamically resist compressive loads, tensile loads, or a combination thereof.

In a particular embodiment, the adjustable interspinous process brace 400 can be injected with one or more injectable biocompatible materials that remain elastic after curing. Further, the injectable biocompatible materials can include polymer materials that remain elastic after curing. Also, the injectable biocompatible materials can include ceramics.

For example, the polymer materials can include polyurethane, polyolefin, silicone, silicone polyurethane copolymers, polymethylmethacrylate, epoxy, cyanoacrylate, hydrogels, or a combination thereof. Further, the polyolefin materials can include polypropylene, polyethylene, halogenated polyolefin, and flouropolyolefin.

The hydrogels can include polyacrylamide (PAAM), poly-N-isopropylacrylamine (PNIPAM), polyvinyl methylether (PVM), polyvinyl alcohol (PVA), polyethyl hydroxyethyl cellulose, poly(2-ethyl)oxazoline, polyethyleneoxide (PEO), polyethylglycol (PEG), polyacrylacid (PAA), polyacrylonitrile (PAN), polyvinylacrylate (PVA), polyvinylpyrrolidone (PVP), or a combination thereof.

In a particular embodiment, the ceramics can include calcium phosphate, hydroxyapatite, calcium sulfate, bioactive glass, or a combination thereof. In an alternative embodiment, the injectable biocompatible materials can include one or more fluids such as sterile water, saline, or sterile air.

In various embodiments, the injection port 418 can include a one-way valve (not shown) to allow passage of injectable material into the interior chamber 416 while substantially preventing expulsion or other movement of the injectable material from the interior chamber 416 through the injection port 418. Further, the injection port 416 can be configured to receive a plug, a screw, a bolt, a dowel, a combination thereof or another similar sealing device (not shown).

Description of a Second Embodiment of an Adjustable Interspinous Process Brace

Figure 6:
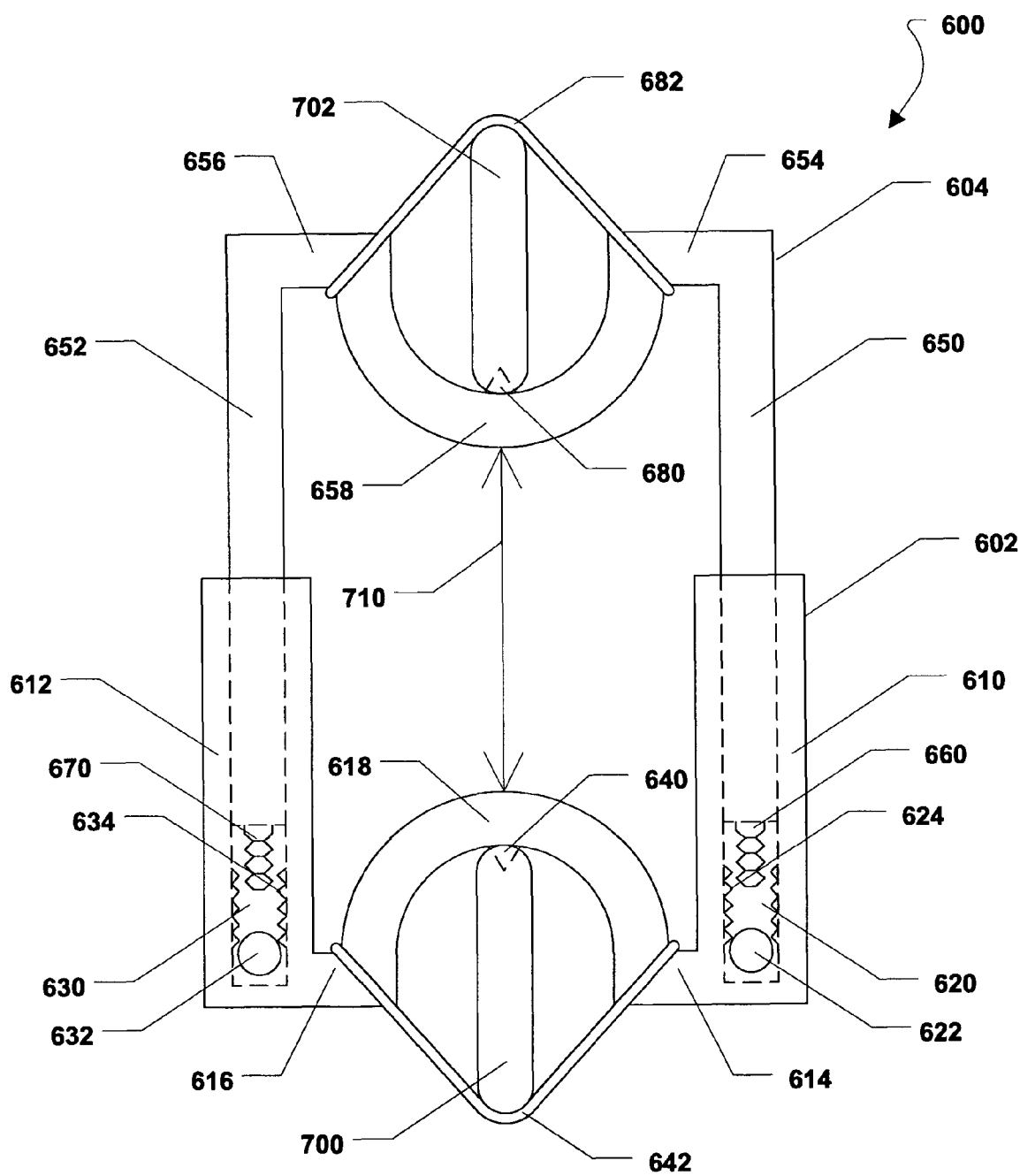
FIG. 6 is a plan view of a second adjustable interspinous process spacer in a retracted position.
Figure 7:
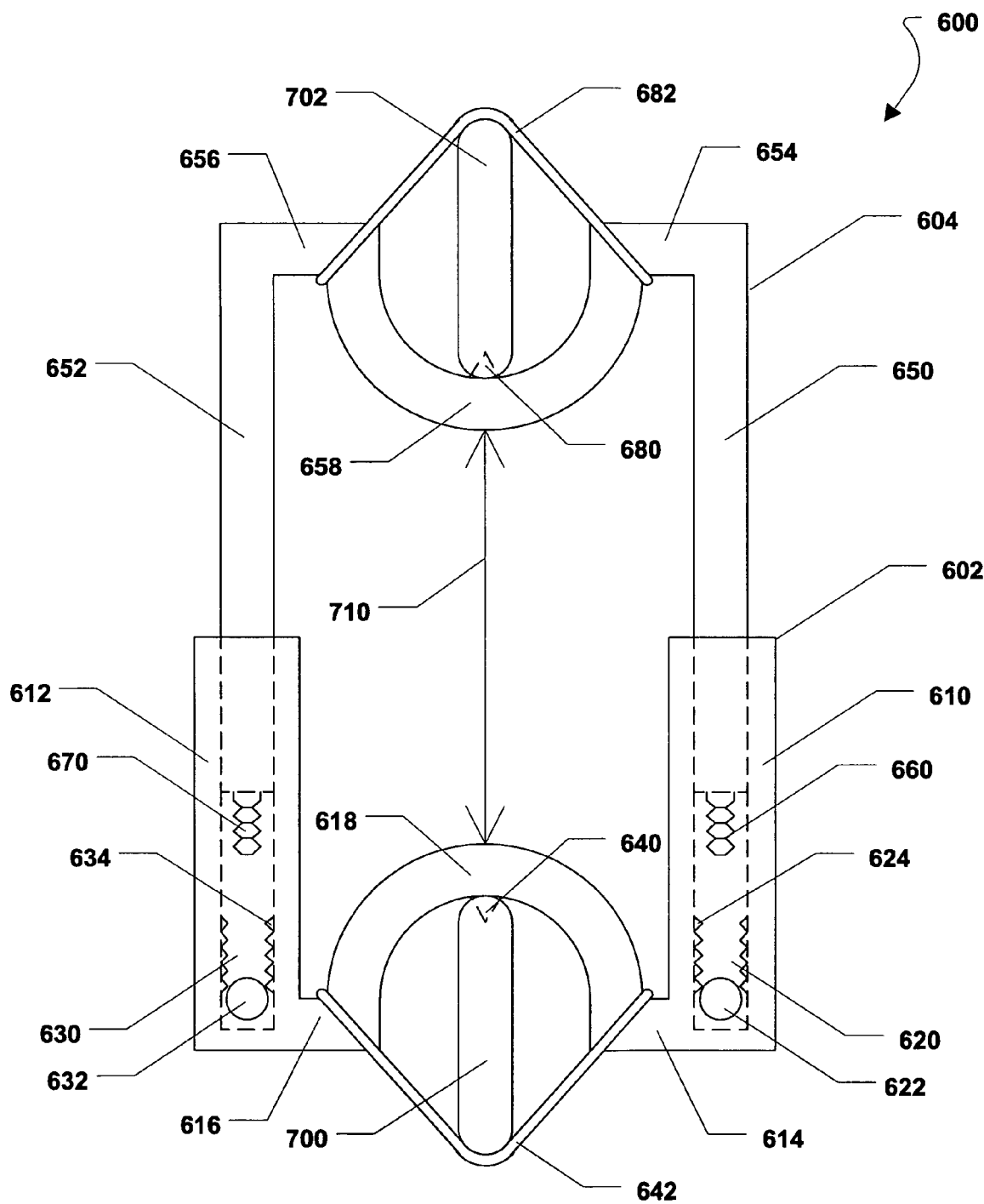
FIG. 7 is a plan view of the second adjustable interspinous process spacer in an extended position.

Referring to FIG. 6 and FIG. 7, a second adjustable interspinous process brace is shown and is generally designated 600. As shown, the adjustable interspinous process brace 600 includes an inferior component 602 and a superior component 604. In a particular embodiment, the components 602, 604 can be made from one or more biocompatible materials. For example, the materials can be metal containing materials, polymer materials, or composite materials that include metals, polymers, or combinations of metals and polymers.

In a particular embodiment, the metal containing materials can be metals. Further, the metal containing materials can be ceramics. Also, the metals can be pure metals or metal alloys. The pure metals can include titanium. Moreover, the metal alloys can include stainless steel, a cobalt-chrome-molybdenum alloy, e.g., ASTM F-999 or ASTM F-75, a titanium alloy, or a combination thereof.

The polymer materials can include polyurethane materials, polyolefin materials, polyaryletherketone (PAEK) materials, silicone materials, hydrogel materials, or a combination thereof. Further, the polyolefin materials can include polypropylene, polyethylene, halogenated polyolefin, flouropolyolefin, or a combination thereof. The polyaryletherketon (PAEK) materials can include polyetherketone (PEK), polyetheretherketone (PEEK), polyetherketoneketone (PEKK), polyetherketoneetherketoneketone (PEKEKK), or a combination thereof. The hydrogels can include polyacrylamide, poly-N-isopropylacrylamine, polyvinyl methylether, polyvinyl alcohol, polyethyl hydroxyethyl cellulose, poly(2-ethyl)oxazoline, polyethyleneoxide, polyethylglycol, polyethylene glycol, polyacrylic acid, polyacrylonitrile, polyvinylacrylate, polyvinylpyrrolidone, or a combination thereof. Alternatively, the components 602, 604 can be made from any other substantially rigid biocompatible materials.

As illustrated in FIG. 6 and FIG. 7, the inferior component 602 can include a first inferior support post 610 and a second inferior support post 612. A first inferior lateral arm 614 can extend from the first inferior support post 610 and a second inferior lateral arm 616 can extend from the second inferior support post 612. Further, an inferior spinous process bracket 618 can extend between the first inferior lateral arm 614 and the second inferior lateral arm 616.

In a particular embodiment, the first inferior support post 610 can be hollow and can include a first interior chamber 620. A lateral cross-section of the first inferior support post 610 can indicate that the first inferior support post 610 can be generally cylindrical. Alternatively, the first inferior support post 610 can have a cross-section that is generally prismatic. Also, the first inferior support post 610 can have any generally polyhedral shape with a central opening, or interior chamber, formed therein. Also, the first inferior support post 610 can include a first injection port 622 established therein. In a particular embodiment, the first injection port 622 can lead to the first interior chamber 620 and can be used to facilitate injection of a material into the first interior chamber 620 of the first inferior support post 610.

FIG. 6 and FIG. 7 show that the first interior chamber 620 within the first inferior support post 610 can include one or more corrugations 624. After a material is injected into the first interior chamber 620 and cured, the corrugations 624 can substantially prevent relative motion between the cured material and the first interior chamber 620.

In a particular embodiment, the second inferior support post 612 can be hollow and can include a second interior chamber 630. A lateral cross-section of the second inferior support post 612 can indicate that the second inferior support post 612 can be generally cylindrical. Alternatively, the second inferior support post 612 can have a cross-section that is generally prismatic. Also, the second inferior support post 612 can have any generally polyhedral shape with a central opening, or interior chamber, formed therein. Also, the second inferior support post 612 can include a second injection port 632 established therein. In a particular embodiment, the second injection port 632 can lead to the second interior chamber 630 and can be used to facilitate injection of a material into the second interior chamber 630 within the second inferior support post 612.

FIG. 6 and FIG. 7 show that the second interior chamber 630 within the second inferior support post 612 can include one or more corrugations 634. After a material is injected into the second interior chamber 630 and cured, the corrugations 634 can substantially prevent relative motion between the cured material and the second interior chamber 630.

As indicated in FIG. 6 and FIG. 7, the inferior spinous process bracket 618 can be generally U shaped. Alternatively, the inferior spinous process bracket 618 can be generally V shaped. Further, the inferior spinous process bracket 618 can include an inferior spinous process engagement structure 640 that extends from the inferior spinous process bracket 618. In a particular embodiment, the inferior spinous process engagement structure 640 can be one or more spikes, one or more teeth, a combination thereof, or some other structure configured to engage a spinous process.

The inferior component 602 can also include an inferior tether 642 that can be wrapped around the inferior component 602, e.g., around the inferior spinous process bracket 618. In particular embodiment, the inferior tether 642 can be looped at least partially around a spinous process and can substantially maintain the spinous process in contact with the inferior spinous process bracket 618. In a particular embodiment, the inferior tether 642 can comprise a biocompatible elastomeric material that flexes during installation and provides a resistance fit against the inferior process. Further, the inferior tether 642 can comprise a substantially non-resorbable suture or the like.

As illustrated in FIG. 6 and FIG. 7, the superior component 604 can include a first superior support post 650 and a second superior support post 652. A first superior lateral arm 654 can extend from the first superior support post 650 and a second superior lateral arm 656 can extend from the second superior support post 652. Further, a superior spinous process bracket 658 can extend between the first superior lateral arm 654 and the second superior lateral arm 656.

In a particular embodiment, the first superior support post 650 can be sized and shaped to fit into the first inferior support post 610. Moreover, a lateral cross-section of the first superior support post 650 can indicate that the first superior support post 650 can be solid and generally cylindrical. Alternatively, the first superior support post 650 can have a cross-section that is generally prismatic. Further, the first superior support post 650 can have any generally polyhedral shape.

FIG. 6 and FIG. 7 indicate that the first superior support post 650 can include a first corrugated tip 660. After a material is injected into the first interior chamber 620 within the first inferior support post 610 and cured, the first corrugated tip 660 can substantially prevent relative motion between the first superior support post 650 and the cured material. Accordingly, the first corrugated tip 660 and the corrugations 624 formed within the first interior chamber 620 can substantially prevent the first superior support post 650 from being withdrawn, or otherwise pulled, from the first interior chamber 624 within the first inferior support post 610.

In a particular embodiment, the second superior support post 652 can be sized and shaped to fit into the second inferior support post 612. Moreover, a lateral cross-section of the second superior support post 652 can indicate that the second superior support post 652 can be solid and generally cylindrical. Alternatively, the second superior support post 652 can have a cross-section that is generally prismatic. Further, the second superior support post 652 can have any generally polyhedral shape.

FIG. 6 and FIG. 7 indicate that the second superior support post 652 can include a second corrugated tip 670. After a material is injected into the second interior chamber 630 within the second inferior support post 612 and cured, the second corrugated tip 670 can substantially prevent relative motion between the second superior support post 652 and the cured material. Accordingly, the second corrugated tip 670 and the corrugations 634 formed within the second interior chamber 630 can substantially prevent the second superior support post 652 from being withdrawn, or otherwise pulled, from the second interior chamber 634 within the second inferior support post 612.

As indicated in FIG. 6 and FIG. 7, the superior spinous process bracket 658 can be generally U shaped. Alternatively, the superior spinous process bracket 658 can be generally V shaped. Further, the superior spinous process bracket 658 can include a superior spinous process engagement structure 680 that extends from the superior spinous process bracket 658. In a particular embodiment, the superior spinous process engagement structure 680 can be one or more spikes, one or more teeth, a combination thereof, or some other structure configured to engage a spinous process.

The superior component 604 can also include a superior tether 682 that can be wrapped around the superior component 604, e.g., around the superior spinous process bracket 658. In particular embodiment, the superior tether 682 can be looped at least partially around a spinous process and can substantially maintain the spinous process in contact with the superior spinous process bracket 658. In a particular embodiment, the superior tether 682 can comprise a biocompatible elastomeric material that flexes during installation and provides a resistance fit against the superior process. Further, the superior tether 682 can comprise a substantially non-resorbable suture or the like.

In a particular embodiment, when the adjustable interspinous process brace 600 is properly installed between a superior vertebra and an inferior vertebra, the inferior spinous process bracket 618 can engage and support an inferior spinous process 700. Further, the superior spinous process bracket 658 can engage and support a superior spinous process 702. More specifically, the inferior spinous process engagement structure 640 can extend slightly into and engage the inferior spinous process 700. Also, the superior spinous process engagement structure 680 can extend slightly into and engage the superior spinous process 702. Accordingly, the spinous process engagement structures 640, 680 and the tethers 642, 682 can substantially prevent the adjustable interspinous process brace 600 from migrating with respect to the spinous processes 700, 702.

Also, in a particular embodiment, the adjustable interspinous process brace 600 can be movable between a retracted position, shown in FIG. 6, and one or more extended positions, shown in FIG. 7. In the retracted position, a distance 710 between the inferior spinous process bracket 618 and the superior spinous process bracket 658 can be at a minimum. However, when a material is injected into the interior chambers 620, 630 within the inferior support posts 610, 612, the distance 710 between the inferior spinous process bracket 618 and the superior spinous process bracket 658 can be greater than when in the retracted position.

Accordingly, the adjustable interspinous process brace 600 can be installed between an inferior spinous process 700 and a superior spinous process 702. Further, the superior component 604 can be moved relative to the inferior component 602, e.g., by injecting material into the interior chambers 620, 630 within the inferior support posts 610, 612, in order to increase the distance between the superior spinous process 702 and the inferior spinous process 700.

Alternatively, a distractor can be used to increase the distance between the superior spinous process 702 and the inferior spinous process 700 and the adjustable interspinous process brace 600 can be adjusted to support the superior spinous process 702 and the inferior spinous process 700. After the adjustable interspinous process brace 600 is adjusted accordingly, the distractor can be removed and the adjustable interspinous process brace 600 can support the superior spinous process 702 and the inferior spinous process 700 to substantially prevent the distance between the superior spinous process 702 and the inferior spinous process 700 from returning to a pre-distraction value. Further, the adjustable interspinous process brace 600 can dynamically resist compressive loads, tensile loads, or a combination thereof.

In a particular embodiment, the adjustable interspinous process brace 600 can be injected with one or more injectable biocompatible materials that remain elastic after curing. Further, the injectable biocompatible materials can include polymer materials that remain elastic after curing. Also, the injectable biocompatible materials can include ceramics.

For example, the polymer materials can include polyurethane, polyolefin, silicone, silicone polyurethane copolymers, polymethylmethacrylate, epoxy, cyanoacrylate, hydrogels, or a combination thereof. Further, the polyolefin materials can include polypropylene, polyethylene, halogenated polyolefin, and flouropolyolefin.

The hydrogels can include polyacrylamide (PAAM), poly-N-isopropylacrylamine (PNIPAM), polyvinyl methylether (PVM), polyvinyl alcohol (PVA), polyethyl hydroxyethyl cellulose, poly(2-ethyl)oxazoline, polyethyleneoxide (PEO), polyethylglycol (PEG), polyacrylacid (PAA), polyacrylonitrile (PAN), polyvinylacrylate (PVA), polyvinylpyrrolidone (PVP), or a combination thereof.

In a particular embodiment, the ceramics can include calcium phosphate, hydroxyapatite, calcium sulfate, bioactive glass, or a combination thereof. In an alternative embodiment, the injectable biocompatible materials can include one or more fluids such as sterile water, saline, or sterile air.

In various embodiments, each or both of the injection ports 622, 632 can include a one-way valve (not shown) to allow passage of injectable material into the interior chambers 620, 630 while substantially preventing expulsion or other movement of the injectable material from the interior chambers 620, 630 through the injection ports 622, 632. Further, the injection ports 622, 632 can be configured to receive a plug, a screw, a bolt, a dowel, a combination thereof or another similar sealing device (not shown).

Description of a Third Embodiment of an Adjustable Interspinous Process Brace

Figure 8:
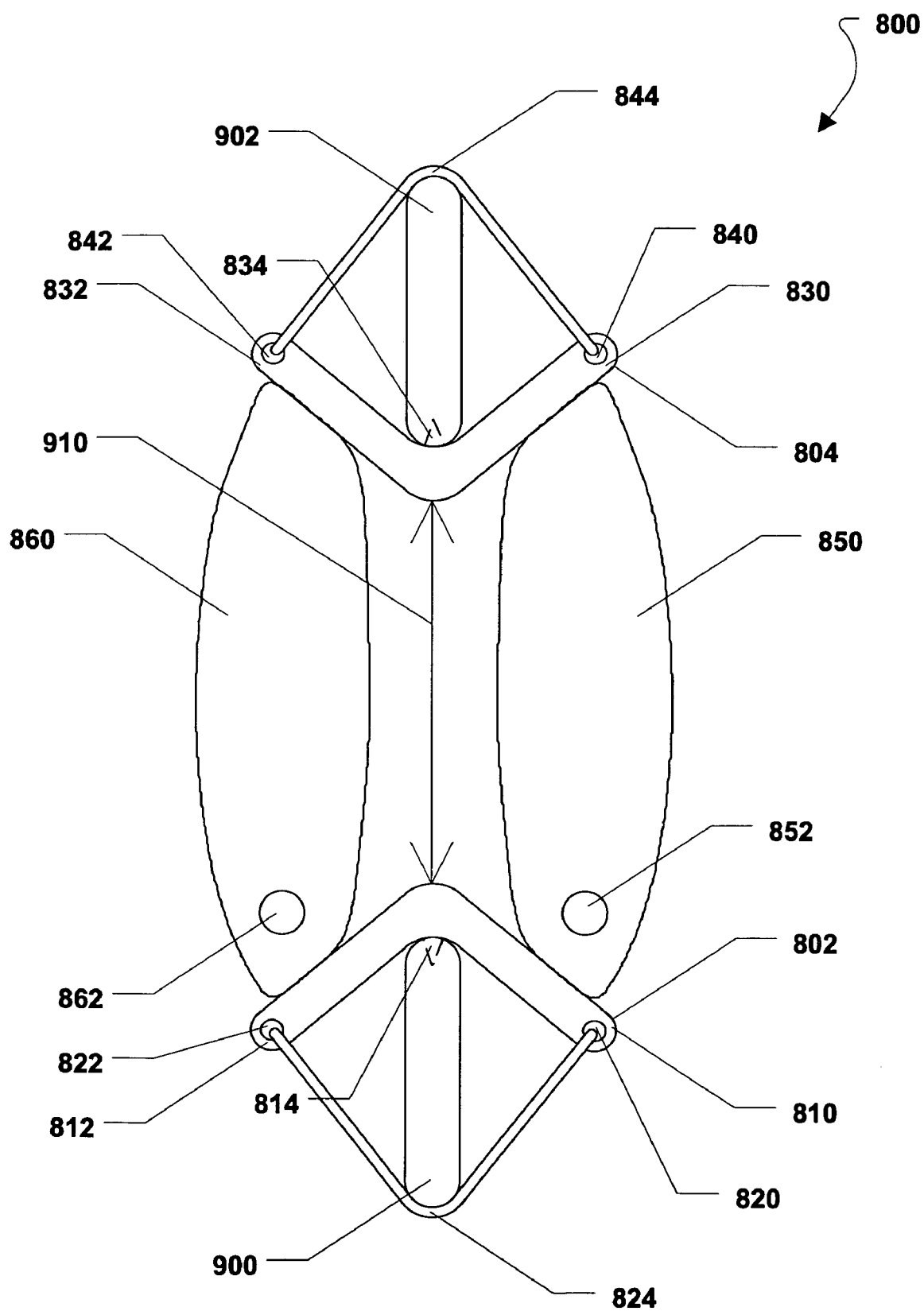
FIG. 8 is a plan view of a third adjustable interspinous process spacer in a retracted position.
Figure 9:
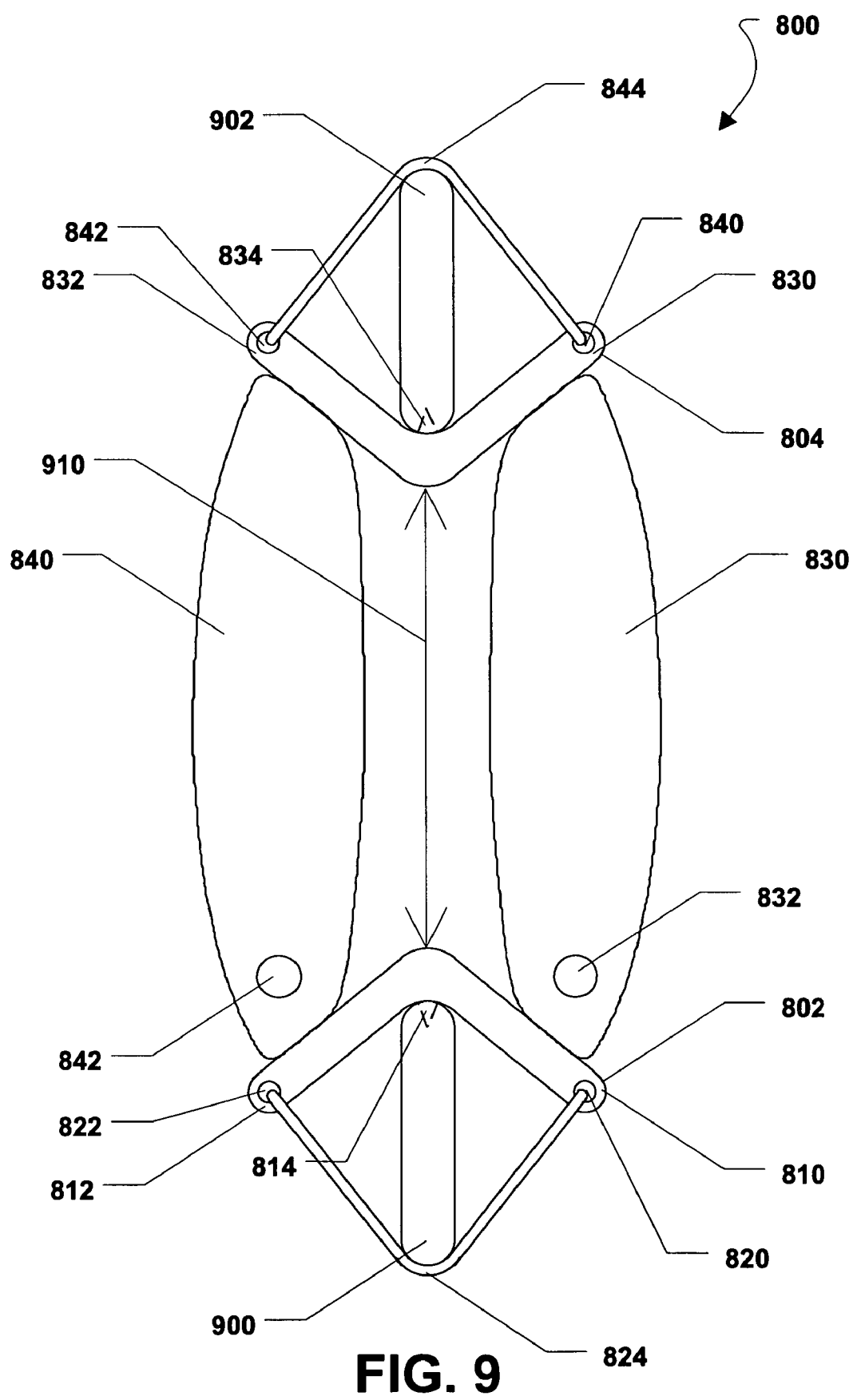
FIG. 9 is a plan view of the third adjustable interspinous process spacer in an extended position.

Referring to FIG. 8 and FIG. 9, a third adjustable interspinous process brace is shown and is generally designated 800. As shown, the adjustable interspinous process brace 800 includes an inferior spinous process bracket 802 and a superior spinous process bracket 804. In a particular embodiment, the brackets 802, 804 can be made from one or more biocompatible materials. For example, the materials can be metal containing materials, polymer materials, or composite materials that include metals, polymers, or combinations of metals and polymers.

In a particular embodiment, the metal containing materials can be metals. Further, the metal containing materials can be ceramics. Also, the metals can be pure metals or metal alloys. The pure metals can include titanium. Moreover, the metal alloys can include stainless steel, a cobalt-chrome-molybdenum alloy, e.g., ASTM F-999 or ASTM F-75, a titanium alloy, or a combination thereof.

The polymer materials can include polyurethane materials, polyolefin materials, polyaryletherketone (PAEK) materials, silicone materials, hydrogel materials, or a combination thereof. Further, the polyolefin materials can include polypropylene, polyethylene, halogenated polyolefin, flouropolyolefin, or a combination thereof. The polyaryletherketon (PAEK) materials can include polyetherketone (PEK), polyetheretherketone (PEEK), polyetherketoneketone (PEKK), polyetherketoneetherketoneketone (PEKEKK), or a combination thereof. The hydrogels can include polyacrylamide, poly-N-isopropylacrylamine, polyvinyl methylether, polyvinyl alcohol, polyethyl hydroxyethyl cellulose, poly(2-ethyl)oxazoline, polyethyleneoxide, polyethylglycol, polyethylene glycol, polyacrylic acid, polyacrylonitrile, polyvinylacrylate, polyvinylpyrrolidone, or a combination thereof. Alternatively, the brackets 802, 804 can be made from any other substantially rigid biocompatible materials.

As indicated in FIG. 8 and FIG. 9, the inferior spinous process bracket 802 can be generally V shaped and can include a first inferior support arm 810 and a second inferior support arm 812. Alternatively, the inferior spinous process bracket 802 can be generally U shaped. Further, the inferior spinous process bracket 802 can include an inferior spinous process engagement structure 814 that extends from the inferior spinous process bracket 802. In a particular embodiment, the inferior spinous process engagement structure 814 can be one or more spikes, one or more teeth, a combination thereof, or some other structure configured to engage a spinous process.

The inferior spinous process bracket 802 can also include a first inferior tether hole 820 and a second inferior tether hole 822. An inferior tether 824 can span the inferior spinous process bracket 802, e.g., between the first inferior tether hole 820 and the second inferior tether hole 822. Further, the inferior tether 824 can be looped at least partially around a spinous process and can substantially maintain the spinous process in contact with the inferior spinous process bracket 802. In a particular embodiment, the inferior tether 824 can comprise a biocompatible elastomeric material that flexes during installation and provides a resistance fit against the inferior process. Further, the inferior tether 824 can comprise a substantially non-resorbable suture or the like.

Further, the superior spinous process bracket 804 can be generally V shaped and can include a first superior support arm 830 and a second superior support arm 832. Alternatively, the superior spinous process bracket 804 can be generally U shaped. The superior spinous process bracket 804 can also include a superior spinous process engagement structure 834 that extends from the superior spinous process bracket 804. In a particular embodiment, the superior spinous process engagement structure 834 can be one or more spikes, one or more teeth, a combination thereof, or some other structure configured to engage a spinous process.

The superior spinous process bracket 804 can also include a first superior tether hole 840 and a second superior tether hole 842. A superior tether 844 can span the superior spinous process bracket 804, e.g., between the first superior tether hole 840 and the second superior tether hole 842. Further, the superior tether 844 can be looped at least partially around a spinous process and can substantially maintain the spinous process in contact with the superior spinous process bracket 804. In a particular embodiment, the superior tether 844 can comprise a biocompatible elastomeric material that flexes during installation and provides a resistance fit against the superior process. Further, the superior tether 844 can comprise a substantially non-resorbable suture or the like.

FIG. 8 and FIG. 9 indicate that the adjustable interspinous process brace 800 can include a first inflatable member 850 disposed between the first inferior support arm 810 and the first superior support arm 830. The first inflatable member 850 can include an injection port 850. Further, the first inflatable member 850 can be inflated via the injection port 852.

Additionally, the adjustable interspinous process brace 800 can include a second inflatable member 860 disposed between the second inferior support arm 812 and the second superior support arm 832. The second inflatable member 860 can include an injection port 862. Further, the second inflatable member 860 can be inflated via the injection port 862.

In a particular embodiment, when the adjustable interspinous process brace 800 is properly installed between a superior vertebra and an inferior vertebra, the inferior spinous process bracket 802 can engage and support an inferior spinous process 900. Further, the superior spinous process bracket 804 can engage and support a superior spinous process 902. More specifically, the inferior spinous process engagement structure 814 can extend slightly into and engage the inferior spinous process 900. Also, the superior spinous process engagement structure 834 can extend slightly into and engage the superior spinous process 902. Accordingly, the spinous process engagement structures 814, 834 and the tethers 824, 844 can substantially prevent the adjustable interspinous process brace 800 from migrating with respect to the spinous processes 900, 902.

Also, in a particular embodiment, the adjustable interspinous process brace 800 can be movable between a collapsed position, shown in FIG. 8, and one or more inflated positions, shown in FIG. 9. In the collapsed position, a distance 910 between the inferior spinous process bracket 802 and the superior spinous process bracket 804 can be at a minimum. However, when a material is injected into the inflatable members 850, 860, the distance 910 between the inferior spinous process bracket 802 and the superior spinous process bracket 804 can be greater than when in the collapsed position.

Accordingly, the adjustable interspinous process brace 800 can be installed between an inferior spinous process 900 and a superior spinous process 902. Further, the superior spinous process bracket 804 can be moved relative to the inferior spinous process bracket 802, e.g., by injecting material into the inflatable members 850, 860, in order to increase the distance between the superior spinous process 902 and the inferior spinous process 900. In various embodiments, the inflatable members 850, 860 can be physically fastened or adhered (e.g., with an adhesive) to the spinous process brackets 802, 804, in order to prevent migration of the inflatable members while in use.

Alternatively, a distractor can be used to increase the distance between the superior spinous process 902 and the inferior spinous process 900 and the adjustable interspinous process brace 800 can be adjusted to support the superior spinous process 902 and the inferior spinous process 900. After the adjustable interspinous process brace 800 is adjusted accordingly, the distractor can be removed and the adjustable interspinous process brace 800 can support the superior spinous process 902 and the inferior spinous process 900 to substantially prevent the distance between the superior spinous process 902 and the inferior spinous process 900 from returning to a pre-distraction value. Further, the adjustable interspinous process brace 800 can dynamically resist compressive loads, tensile loads, or a combination thereof.

In a particular embodiment, the adjustable interspinous process brace 800 can be injected with one or more injectable biocompatible materials that remain elastic after curing. Further, the injectable biocompatible materials can include polymer materials that remain elastic after curing. Also, the injectable biocompatible materials can include ceramics.

For example, the polymer materials can include polyurethane, polyolefin, silicone, silicone polyurethane copolymers, polymethylmethacrylate, epoxy, cyanoacrylate, hydrogels, or a combination thereof. Further, the polyolefin materials can include polypropylene, polyethylene, halogenated polyolefin, and flouropolyolefin.

The hydrogels can include polyacrylamide (PAAM), poly-N-isopropylacrylamine (PNIPAM), polyvinyl methylether (PVM), polyvinyl alcohol (PVA), polyethyl hydroxyethyl cellulose, poly(2-ethyl)oxazoline, polyethyleneoxide (PEO), polyethylglycol (PEG), polyacrylacid (PAA), polyacrylonitrile (PAN), polyvinylacrylate (PVA), polyvinylpyrrolidone (PVP), or a combination thereof.

In a particular embodiment, the ceramics can include calcium phosphate, hydroxyapatite, calcium sulfate, bioactive glass, or a combination thereof. In an alternative embodiment, the injectable biocompatible materials can include one or more fluids such as sterile water, saline, or sterile air.

In various embodiments, each or both injection ports 852, 862 can include a one-way valve (not shown) to allow passage of injectable material into the inflatable members 850, 860 while substantially preventing expulsion or other movement of the injectable material from the inflatable members 850, 860 through the injection ports 852, 862. Further, the injection ports 852, 862 can be configured to receive a plug, a screw, a bolt, a dowel, a combination thereof or another similar sealing device (not shown).

Description of a First Method of Treating a Spine

Figure 10:
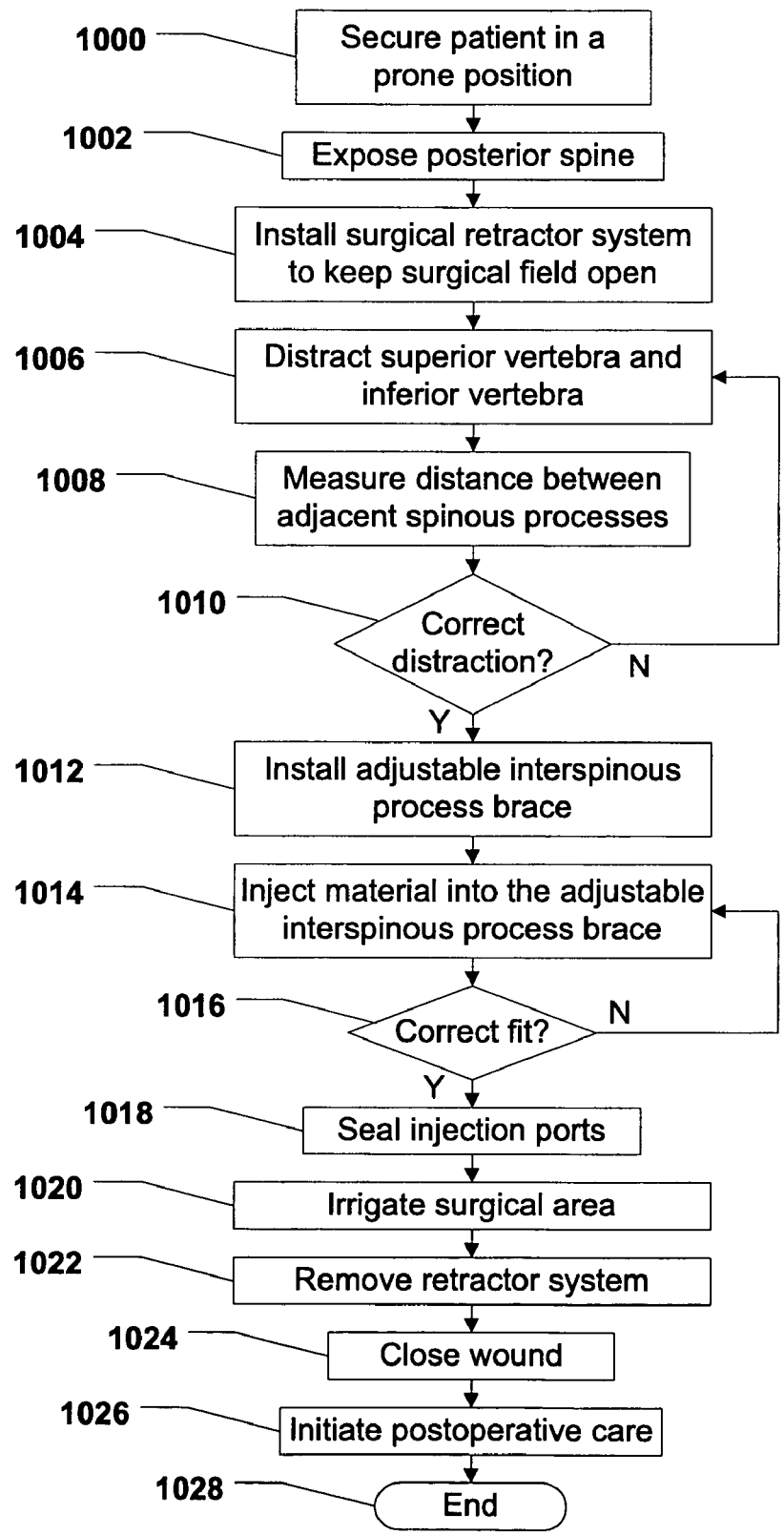
FIG. 10 is a flow chart illustrating a first method of treating a spine.

Referring to FIG. 10, a method of treating a spine is shown and commences at block 1000. At block 1000, a patient can be secured in a prone position, e.g., on an operating table. At block 1002, the posterior spine can be exposed in order to expose adjacent spinous processes. Further, at block 1004, a surgical retractor system can be installed to keep a surgical field open.

Moving to block 1006, a superior vertebra and inferior vertebra can be distracted. In a particular embodiment, the superior vertebra and inferior vertebra can be distracted using a distractor. At block 1008, a distance between the adjacent spinous processes can be measured. Thereafter, at block 1010 it is determined whether the distraction is correct, e.g., has the superior vertebra and inferior vertebral been distracted such that a distance between the adjacent spinous processes has reached a value that a surgeon has deemed therapeutic. For example, the superior vertebra and inferior vertebra can be distracted in order to reduce or obviate impingement on a nerve root.

If the distraction is not correct, the method can return to block 1006 and the superior vertebra and inferior vertebra can be further distracted. Conversely, if the distraction is correct, the method can move to block 1012 and an adjustable interspinous process brace can be installed between the adjacent spinous processes.

Proceeding to block 1014, a material can be injected into the adjustable interspinous process brace. In a particular embodiment, the adjustable interspinous process brace can be injected with one or more injectable biocompatible materials that remain elastic after curing. Further, the injectable biocompatible materials can include polymer materials that remain elastic after curing. Also, the injectable biocompatible materials can include ceramics.

For example, the polymer materials can include polyurethane, polyolefin, silicone, silicone polyurethane copolymers, polymethylmethacrylate, epoxy, cyanoacrylate, hydrogels, or a combination thereof. Further, the polyolefin materials can include polypropylene, polyethylene, halogenated polyolefin, and flouropolyolefin.

The hydrogels can include polyacrylamide (PAAM), poly-N-isopropylacrylamine (PNIPAM), polyvinyl methylether (PVM), polyvinyl alcohol (PVA), polyethyl hydroxyethyl cellulose, poly(2-ethyl)oxazoline, polyethyleneoxide (PEO), polyethylglycol (PEG), polyacrylacid (PAA), polyacrylonitrile (PAN), polyvinylacrylate (PVA), polyvinylpyrrolidone (PVP), or a combination thereof.

In a particular embodiment, the ceramics can include calcium phosphate, hydroxyapatite, calcium sulfate, bioactive glass, or a combination thereof. In an alternative embodiment, the injectable biocompatible materials can include one or more fluids such as sterile water, saline, or sterile air.

Moving to decision step 1016 it can be determined whether the adjustable interspinous process brace fits correctly into the space between the adjacent spinous processes. If not, the method can return to block 1014 and more material can be injected into the adjustable interspinous process brace. On the other hand, if the adjustable interspinous process brace fits correctly between the adjacent spinous processes, the method can proceed to block 1018.

At block 1018, one or more injection ports can be sealed. In a particular embodiment, simply curing the material within the adjustable interspinous process brace can seal the one or more injection ports. Alternatively, a plug, a screw, a bolt, a dowel, a combination thereof, or another similar device can be used to seal the one or more injection ports. Further, a one-way valve can be incorporated into each injection port and can allow material to be injected into the adjustable interspinous process brace, but prevent the same material from being expelled from the adjustable interspinous process brace.

Continuing to block 1020, the surgical area can be irrigated. At block 1022, the retractor system can be removed. Further, at block 1024, the surgical wound can be closed. The surgical wound can be closed by simply allowing the patient's skin to close due to the elasticity of the skin. Alternatively, the surgical wound can be closed using sutures, surgical staples, or any other suitable surgical technique well known in the art. At block 1026, postoperative care can be initiated. The method can end at state 1028.

Figure 11:
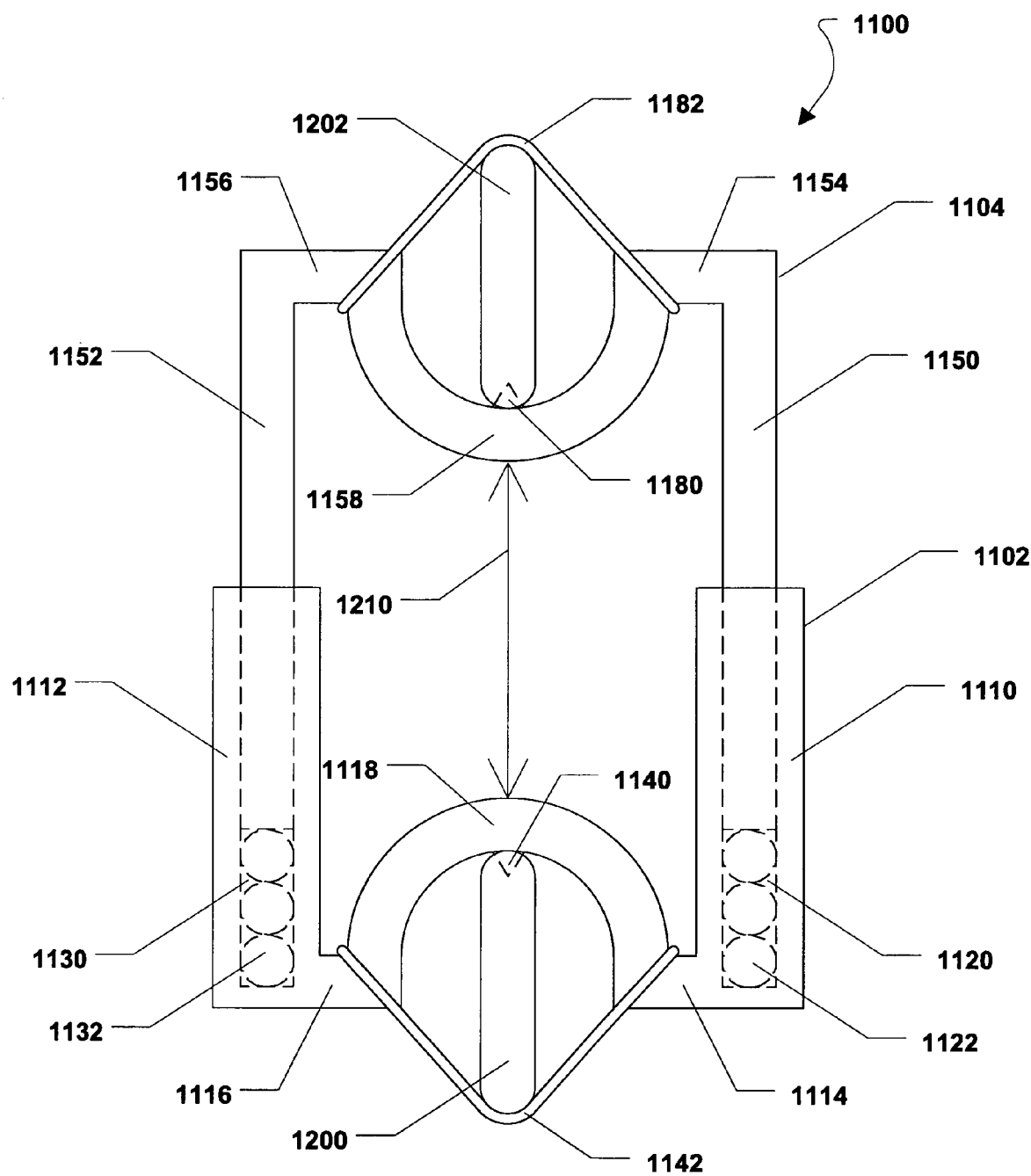
FIG. 11 is a plan view of a fourth adjustable interspinous process spacer in a retracted position.
Figure 12:
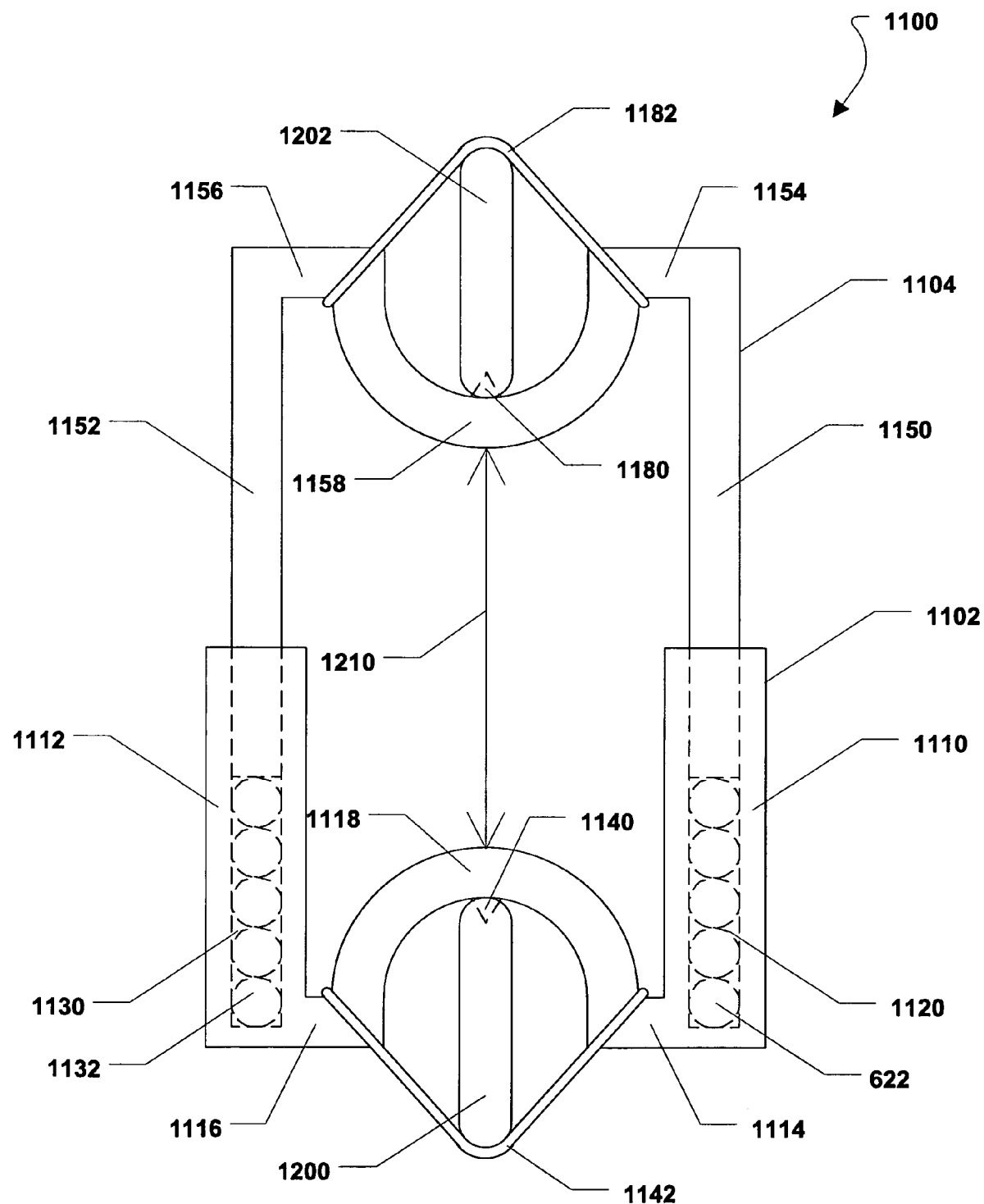
FIG. 12 is a plan view of the fourth adjustable interspinous process spacer in an extended position.

Description of a Fourth Embodiment of an Adjustable Interspinous Process Brace Referring to FIG. 11 and FIG. 12, a fourth adjustable interspinous process brace is shown and is generally designated 1100. As shown, the adjustable interspinous process brace 1100 includes an inferior component 1102 and a superior component 1104. In a particular embodiment, the components 1102, 1104 can be made from one or more biocompatible materials. For example, the materials can be metal containing materials, polymer materials, or composite materials that include metals, polymers, or combinations of metals and polymers.

In a particular embodiment, the metal containing materials can be metals. Further, the metal containing materials can be ceramics. Also, the metals can be pure metals or metal alloys. The pure metals can include titanium. Moreover, the metal alloys can include stainless steel, a cobalt-chrome-molybdenum alloy, e.g., ASTM F-999 or ASTM F-75, a titanium alloy, or a combination thereof.

The polymer materials can include polyurethane materials, polyolefin materials, polyaryletherketone (PAEK) materials, silicone materials, hydrogel materials, or a combination thereof. Further, the polyolefin materials can include polypropylene, polyethylene, halogenated polyolefin, flouropolyolefin, or a combination thereof. The polyaryletherketon (PAEK) materials can include polyetherketone (PEK), polyetheretherketone (PEEK), polyetherketoneketone (PEKK), polyetherketoneetherketoneketone (PEKEKK), or a combination thereof. The hydrogels can include polyacrylamide, poly-N-isopropylacrylamine, polyvinyl methylether, polyvinyl alcohol, polyethyl hydroxyethyl cellulose, poly(2-ethyl)oxazoline, polyethyleneoxide, polyethylglycol, polyethylene glycol, polyacrylic acid, polyacrylonitrile, polyvinylacrylate, polyvinylpyrrolidone, or a combination thereof. Alternatively, the components 1102, 1104 can be made from any other substantially rigid biocompatible materials.

As illustrated in FIG. 11 and FIG. 12, the inferior component 1102 can include a first inferior support post 1110 and a second inferior support post 1112. A first inferior lateral arm 1114 can extend from the first inferior support post 1110 and a second inferior lateral arm 1116 can extend from the second inferior support post 1112. Further, an inferior spinous process bracket 1118 can extend between the first inferior lateral arm 1114 and the second inferior lateral arm 1116.

In a particular embodiment, the first inferior support post 1110 can be hollow and can include a first interior chamber 1120. A lateral cross-section of the first inferior support post 1110 can indicate that the first inferior support post 1110 can be generally cylindrical. Alternatively, the first inferior support post 1110 can have a cross-section that is generally prismatic. Also, the first inferior support post 1110 can have any generally polyhedral shape with a central opening, or interior chamber, formed therein.

As shown in FIG. 11 and FIG. 12, one or more spacers 1122 can be disposed within the first interior chamber 1120. In a particular embodiment, the spacers 1122 can be elastic. Further, the spacers 1122 can be spherically shaped, cube shaped, disc shaped, or a combination thereof.

In a particular embodiment, the second inferior support post 1112 can be hollow and can include a second interior chamber 1130. A lateral cross-section of the second inferior support post 1112 can indicate that the second inferior support post 1112 can be hollow and generally cylindrical. Alternatively, the second inferior support post 1112 can have a cross-section that is generally prismatic. Also, the second inferior support post 1112 can have any generally polyhedral shape with a central opening, or interior chamber, formed therein.

As shown in FIG. 11 and FIG. 12, one or more spacers 1132 can be disposed within the first interior chamber 1130. In a particular embodiment, the spacers 1132 can be elastic. Further, the spacers 1132 can be spherically shaped, cube shaped, disc shaped, or a combination thereof.

As indicated in FIG. 11 and FIG. 12, the inferior spinous process bracket 1118 can be generally U shaped. Alternatively, the inferior spinous process bracket 1118 can be generally V shaped. Further, the inferior spinous process bracket 1118 can include an inferior spinous process engagement structure 1140 that extends from the inferior spinous process bracket 1118. In a particular embodiment, the inferior spinous process engagement structure 1140 can be one or more spikes, one or more teeth, a combination thereof, or some other structure configured to engage a spinous process.

The inferior component 1102 can also include an inferior tether 1142 that can be wrapped around the inferior component 1102, e.g., around the inferior spinous process bracket 1118. In particular embodiment, the inferior tether 1142 can be looped at least partially around a spinous process and can substantially maintain the spinous process in contact with the inferior spinous process bracket 1118. In a particular embodiment, the inferior tether 1142 can comprise a biocompatible elastomeric material that flexes during installation and provides a resistance fit against the inferior process. Further, the inferior tether 1142 can comprise a substantially non-resorbable suture or the like.

As illustrated in FIG. 11 and FIG. 12, the superior component 1104 can include a first superior support post 1150 and a second superior support post 1152. A first superior lateral arm 1154 can extend from the first superior support post 1150 and a second superior lateral arm 1156 can extend from the second superior support post 1152. Further, a superior spinous process bracket 1158 can extend between the first superior lateral arm 1154 and the second superior lateral arm 1156.

In a particular embodiment, the first superior support post 1150 can be sized and shaped to fit into the first inferior support post 1110. Moreover, a lateral cross-section of the first superior support post 1150 can indicate that the first superior support post 1150 can be solid and generally cylindrical. Alternatively, the first superior support post 1150 can have a cross-section that is generally prismatic. Further, the first superior support post 1150 can have any generally polyhedral shape.

In a particular embodiment, the second superior support post 1152 can be sized and shaped to fit into the second inferior support post 1112. Moreover, a lateral cross-section of the second superior support post 1152 can indicate that the second superior support post 1152 can be solid and generally cylindrical. Alternatively, the second superior support post 1152 can have a cross-section that is generally prismatic. Further, the second superior support post 1152 can have any generally polyhedral shape.

As indicated in FIG. 11 and FIG. 12, the superior spinous process bracket 1158 can be generally U shaped. Alternatively, the superior spinous process bracket 1158 can be generally V shaped. Further, the superior spinous process bracket 1158 can include a superior spinous process engagement structure 1180 that extends from the superior spinous process bracket 1158. In a particular embodiment, the superior spinous process engagement structure 1180 can be one or more spikes, one or more teeth, a combination thereof, or some other structure configured to engage a spinous process.

The superior component 1104 can also include a superior tether 1182 that can be wrapped around the superior component 1104, e.g., around the superior spinous process bracket 1158. In particular embodiment, the superior tether 1182 can be looped at least partially around a spinous process and can substantially maintain the spinous process in contact with the superior spinous process bracket 1158. In a particular embodiment, the superior tether 1182 can comprise a biocompatible elastomeric material that flexes during installation and provides a resistance fit against the superior process. Further, the superior tether 1182 can comprise a substantially non-resorbable suture or the like.

In a particular embodiment, when the adjustable interspinous process brace 1100 is properly installed between a superior vertebra and an inferior vertebra, the inferior spinous process bracket 1118 can engage and support an inferior spinous process 1200. Further, the superior spinous process bracket 1158 can engage and support a superior spinous process 1202. More specifically, the inferior spinous process engagement structure 1140 can extend slightly into and engage the inferior spinous process 1200. Also, the superior spinous process engagement structure 1180 can extend slightly into and engage the superior spinous process 1202. Accordingly, the spinous process engagement structures 1140, 1180 and the tethers 1142, 1182 can substantially prevent the adjustable interspinous process brace 1100 from migrating with respect to the spinous processes 1200, 1202.

Also, in a particular embodiment, the adjustable interspinous process brace 1100 can be movable between a retracted position, shown in FIG. 11, and one or more extended positions, shown in FIG. 12. In the retracted position, a distance 1210 between the inferior spinous process bracket 1118 and the superior spinous process bracket 1158 can be minimized. However, when spacers 1122, 1132 are installed, or otherwise disposed, within the interior chambers 1120, 1130 of the inferior support posts 1110, 1112, the distance 1210 between the inferior spinous process bracket 1118 and the superior spinous process bracket 1158 can be greater than when in the retracted position.

Accordingly, a distractor can be used to increase the distance between the superior spinous process 1202 and the inferior spinous process 1200 and the adjustable interspinous process brace 1100 can be adjusted to support the superior spinous process 1202 and the inferior spinous process 1200, e.g., by placing spacers 1122, 1132 into the interior chambers 1120, 1130. After the adjustable interspinous process brace 1100 is adjusted accordingly, the distractor can be removed and the adjustable interspinous process brace 1100 can support the superior spinous process 1202 and the inferior spinous process 1200 and substantially prevent the distance between the superior spinous process 1202 and the inferior spinous process 1200 from returning to a pre-distraction value.

Description of a Second Method of Treating a Spine

Figure 13:
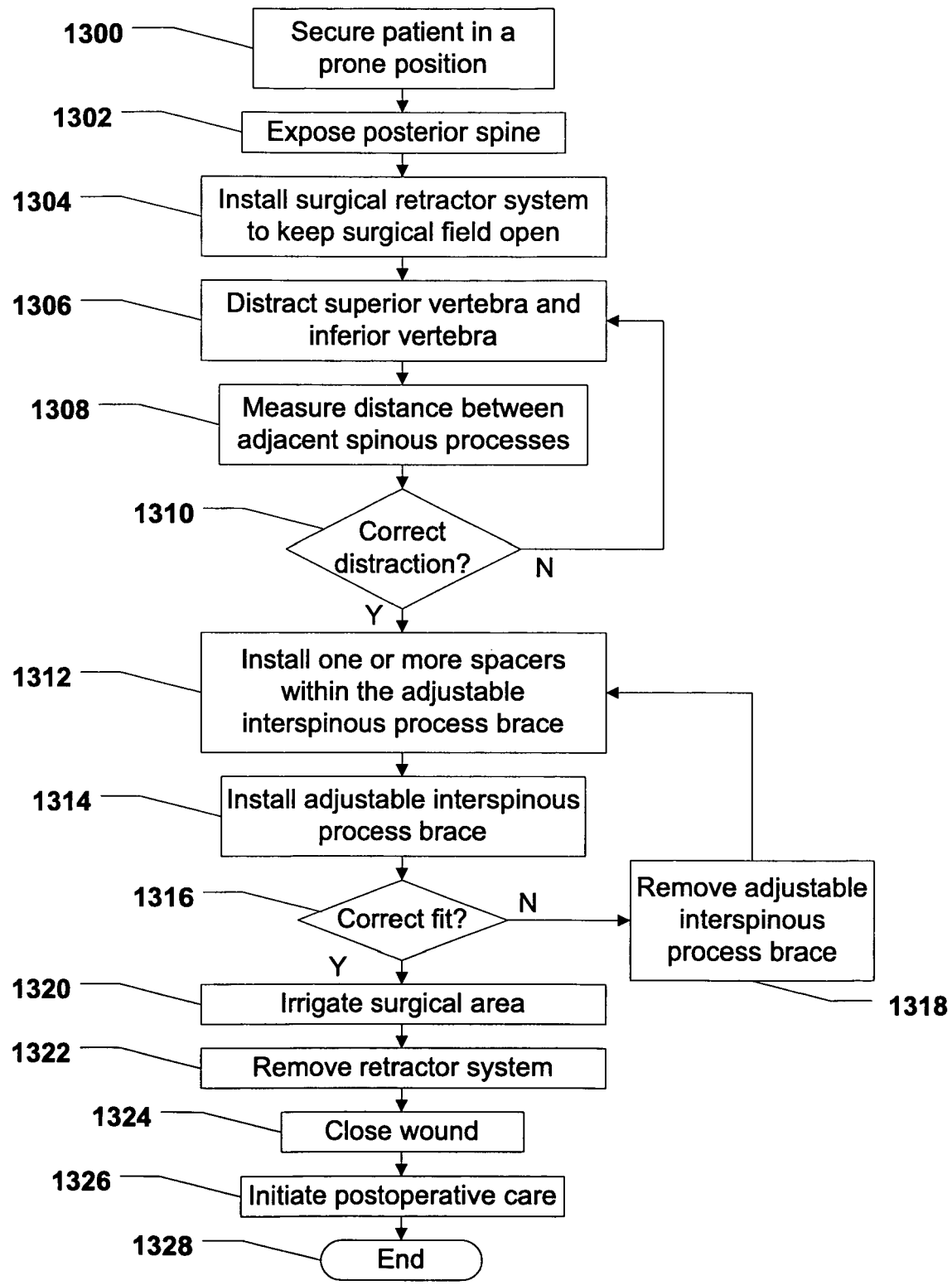
FIG. 13 is a flow chart illustrating a second method of treating a spine.

Referring to FIG. 13, a method of treating a spine is shown and commences at block 1300. At block 1300, a patient can be secured in a prone position, e.g., on an operating table. At block 1302, the posterior spine can be exposed in order to expose adjacent spinous processes. Further, at block 1304, a surgical retractor system can be installed to keep a surgical field open.

Moving to block 1306, a superior vertebra and inferior vertebra can be distracted. In a particular embodiment, the superior vertebra and inferior vertebra can be distracted using a distractor. At block 1308, a distance between the adjacent spinous processes can be measured. Thereafter, at block 1310 it is determined whether the distraction is correct, e.g., has the superior vertebra and inferior vertebral been distracted such that a distance between the adjacent spinous processes has reached a value that a surgeon has deemed therapeutic. For example, the superior vertebra and inferior vertebra can be distracted in order to reduce impingement on a nerve root.

If the distraction is not correct, the method can return to block 1306 and the superior vertebra and inferior vertebra can be further distracted. Conversely, if the distraction is correct, the method can move to block 1312 and one or more spaces can be installed within an adjustable interspinous process brace. In a particular embodiment, the spacers can be elastic. Further, the spacers can be spherically shaped, cube shaped, disc shaped, or a combination thereof.

At block 1314, the adjustable interspinous process brace can be installed between the adjacent spinous processes. Thereafter, at decision step 1316, it can be determined whether the adjustable interspinous process brace fits correctly into the space between the adjacent spinous processes. If not, the method proceed to block 1318 and the adjustable interspinous process brace can be removed from between the adjacent interspinous processes. The method can then return to block 1312 and one or more additional spacers can be installed within the adjustable interspinous process brace. On the other hand, if the adjustable interspinous process brace fits correctly between the adjacent spinous processes, the method can proceed to block 1320.

At block 1320, the surgical area can be irrigated. At block 1322, the retractor system can be removed. Further, at block 1324, the surgical wound can be closed. The surgical wound can be closed by simply allowing the patient's skin to close due to the elasticity of the skin. Alternatively, the surgical wound can be closed using sutures, surgical staples, or any other suitable surgical technique well known in the art. At block 1326, postoperative care can be initiated. The method can end at state 1328.

CONCLUSION

With the configuration of structure described above, the adjustable interspinous process brace provides a device that can be used to treat a spine and substantially alleviate or minimize one or more symptoms associated with disc degeneration, facet joint degeneration, or a combination thereof. For example, the adjustable interspinous process brace can installed between adjacent spinous processes in order to support the spinous processes and maintain them at or near a predetermined distance there between.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An adjustable interspinous process brace, comprising:
    a first component having a first post extending along a longitudinal axis of the brace and a first spinous process bracket configured to receive a first spinous process, the first spinous process bracket comprising an outwardly facing concave surface;

the first spinous process bracket extending outwardly from the first post such that the first spinous process bracket is spaced away from the first post and from the longitudinal axis;

a second component having a second post extending along the longitudinal axis and a second spinous process bracket configured to receive a second spinous process adjacent to the first spinous process, the second spinous process bracket comprising an outwardly facing concave surface;

the second spinous process bracket extending outwardly from the second post such that the second spinous process bracket is spaced away from the second post and from the longitudinal axis;

the first post having an interior chamber therein configured to receive an injectable fluid;

wherein the first component is movably engaged with respect to the second component from a retracted position to an extended position in which a distance between the first spinous process bracket and the second spinous process bracket is increased;

wherein when the injectable fluid is received in the chamber, the injectable fluid inhibits movement of the first and second components from the extended position toward the retracted position;

wherein when the first spinous process bracket receives the first spinous process and the second spinous process bracket receives the second spinous process, the longitudinal axis extends parallel to a sagittal plane defined by the spinous processes.

2. The adjustable interspinous process brace of claim 1 further comprising a first spinous process engagement structure projecting from the first spinous process bracket in a direction generally opposite the second spinous process bracket.

3. The adjustable interspinous process brace of claim 1 wherein the second post slidably engages the first post in a telescopic fashion and extends into the interior chamber of the first post.

4. The adjustable interspinous process brace of claim 3 further comprising a second spinous process engagement structure projecting from the second spinous process bracket in a direction generally opposite the first spinous process bracket.

5. The adjustable interspinous process brace of claim 3 further comprising the injectable fluid disposed in the interior chamber; wherein the injectable fluid supports the second post and substantially prevents the second post from withdrawing from the interior chamber of the first post.

6. The adjustable interspinous process brace of claim 5 wherein the injectable fluid comprises a polymer, a ceramic, or a combination thereof.

7. The adjustable interspinous process brace of claim 6, wherein the polymer comprises polyurethane, polyolefin, silicone, silicone polyurethane copolymers, polymethylmethacrylate, epoxy, cyanoacrylate, hydrogel, or a combination thereof.

8. The adjustable interspinous process brace of claim 7, wherein the polyolefin comprises polypropylene, polyethylene, halogenated polyolefin, flouropolyolefin, or a combination thereof.

9. The adjustable interspinous process brace of claim 7, wherein the hydrogel comprises polyacrylamide (PAAM), poly-N-isopropylacrylamine (PNIPAM), polyvinyl methylether (PVM), polyvinyl alcohol (PVA), polyethyl hydroxyethyl cellulose, poly (2-ethyl) oxazoline, polyethyleneoxide (PEO), polyethylglycol (PEG), polyacrylacid (PAA), polyacrylonitrile (PAN), polyvinylacrylate (PVA), polyvinylpyrrolidone (PVP), or a combination thereof.

10. The adjustable interspinous process brace of claim 6, wherein the ceramic comprises calcium phosphate, hydroxyapatite, calcium sulfate, bioactive glass, or a combination thereof.

11. The adjustable interspinous process brace of claim 3 further comprising the injectable fluid disposed in the interior chamber; wherein the interior chamber comprises a corrugation configured to engage the injectable fluid.

12. The adjustable interspinous process brace of claim 11 wherein the second post comprises a corrugated tip configured to engage the injectable fluid.

13. The adjustable interspinous process brace of claim 1 further comprising the injectable fluid disposed in the interior chamber; wherein the injectable fluid comprises sterile water, saline, or sterile air.

14. The adjustable interspinous process brace of claim 1 wherein the first post includes a first hole transverse to the longitudinal axis; wherein the second post includes a plurality of spaced apart second holes transverse to the longitudinal axis; and further comprising a locking pin disposable through said first hole and one of the second holes to inhibit movement of the first and second components relative to each other.

* * * * *